United States Patent
Coady et al.

(10) Patent No.: US 9,469,726 B2
(45) Date of Patent: Oct. 18, 2016

(54) WATER SOLUBLE POLYCARBONATES FOR MEDICAL APPLICATIONS

(71) Applicants: International Business Machines Corporation, Armonk, NY (US); Agency For Science, Technology and Research, Singapore (SG)

(72) Inventors: Daniel J. Coady, San Jose, CA (US); Amanda C. Engler, San Jose, CA (US); James L. Hedrick, Pleasanton, CA (US); Xiyu Ke, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 14/506,733

(22) Filed: Oct. 6, 2014

(65) Prior Publication Data

US 2016/0095933 A1 Apr. 7, 2016

(51) Int. Cl.
| | | |
|---|---|---|
| *A61K 47/48* | (2006.01) | |
| *A61K 45/06* | (2006.01) | |
| *A61K 9/14* | (2006.01) | |
| *C08G 64/18* | (2006.01) | |
| *C08G 64/42* | (2006.01) | |

(52) U.S. Cl.
CPC .............. *C08G 64/18* (2013.01); *A61K 9/146* (2013.01); *A61K 45/06* (2013.01); *C08G 64/42* (2013.01)

(58) Field of Classification Search
CPC . A61K 31/785; A61K 31/80; C08G 64/0241
See application file for complete search history.

(56) References Cited

U.S. PATENT DOCUMENTS

| 7,951,899 B2 | 5/2011 | Gross et al. | |
|---|---|---|---|
| 8,143,369 B2 | 3/2012 | Fujiwara et al. | |
| 2010/0196482 A1* | 8/2010 | Radovic-Moreno . | A61K 47/488 424/487 |
| 2010/0280219 A1 | 11/2010 | Cooley et al. | |
| 2010/0305281 A1 | 12/2010 | Fujiwara et al. | |
| 2015/0157723 A1 | 6/2015 | Chan et al. | |

FOREIGN PATENT DOCUMENTS

JP 2013527280 A 6/2013

OTHER PUBLICATIONS

Jung et al (A. Am. Chem. Soc, 2003, vol. 125, 5351-5355 2003).*
Delcroix, et al. "Ring-Opening Polymerization of Trimethylene Carbonate Catalyzed by Methanesulfonic Acid: Activated Monomer versus Active Chain End Mechanisms", Macromolecules 2010, 43, pp. 8828-8835; Published on Web Oct. 13, 2010.
Engler, et al., "Accessing New Materials through Polymerization and Modification of a Polycarbonate with a Pendant Activated Ester", Macromolecules 2013, 46, 1283-1290; Published: Feb. 7, 2013.
Kataoka, et al. "Block copolymer micelles for drug delivery: design, characterization and biological significance", Advanced Drug Delivery Reviews 47 (2001) 113-131.
Knop, et al., "Poly(ethylene glycol) in Drug Delivery: Pros and Cons as Well as Potential Alternatives", Angew. Chem. Int. Ed. 2010, 49, 6288-6308.
Kojima, et al., "Synthe s i s of Polyamidoamine Dendrimers Having Poly(ethylene glycol) Grafts and Their Ability to Encapsulate Anticancer Drugs", Bioconjugate Chem. 2000, 11, 910-917; Published on Web Nov. 1, 2000.
Li, et al., "PEGylated PLGA nanoparticles as protein carriers: synthesis, preparation and biodistribution in rats", Journal of Controlled Release 71 (2001) 203-211.
Liu, et al., "Synthesis and Characterization of Novel Aliphatic Polycarbonates Bearing Pendant Allyl Ether Groups", Chinese Chemical Letters vol. 17, No. 1, pp. 137-139, 2006.
Sanders, et al., "A Simple and Efficient Synthesis of Functionalized Cyclic Carbonate Monomers Using a Versatile Pentafluorophenyl Ester Intermediate", J. Am. Chem. Soc. 2010, 132, 14724-14726; Published on Web Sep. 30, 2010.
Zhou, et al., "Synthesis and Characterization of Novel Aliphatic Poly(carbonate-ester)s with Functional Pendent Groups", Macromol. Rapid Commun. 2005, 26, 1309-1314.
Engler, et al., "Hydrophilic Polycarbonates: Promising Degradable Alternatives to Poly(ethylene glycol)-Based Stealth Materials", Macromolecules 2015, 48, 11673-1678; Published: Mar. 4, 2015.
Japanese Patent Office, International Search Report and Written Opinion mailed Oct. 13, 2015; International application No. PCT/IB2015/056639, filed Sep. 1, 2015.

* cited by examiner

*Primary Examiner* — Anna Falkowitz
(74) *Attorney, Agent, or Firm* — Michael R. Roberts

(57) ABSTRACT

Water soluble biodegradable polymers were prepared by an organoacid catalyzed ring opening polymerization (ROP) of a cyclic carbonate monomer bearing an active ester side chain. The initial polymer comprising an active ester side chain was treated with an amino-alcohol, which transformed the active ester groups to N-substituted amide groups bearing mono-hydroxy alkyl groups and/or dihydroxy alkyl groups, thereby forming the water soluble polymers. The water-soluble polymers are non-toxic and exhibit stealth properties in buffered serum solution.

36 Claims, 10 Drawing Sheets

WATER SOLUBLE POLYCARBONATES FOR MEDICAL APPLICATIONS

PARTIES TO A JOINT RESEARCH AGREEMENT

This invention was made under a joint research agreement between International Business Machines Corporation and the Agency For Science, Technology and Research.

BACKGROUND

The present invention relates to water soluble polycarbonates for medical applications, and more specifically to water soluble polycarbonates for controlled delivery of therapeutic agents such as drugs.

Poly(ethylene glycol) (PEG), which has the structure

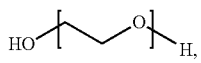

is the standard for synthetic water-soluble polymers used for therapeutic delivery. PEG is synthesized by a ring opening polymerization of ethylene oxide. In general, PEG can have a wide range of molecular weights and a narrow polydispersity index (PDI). PEG is soluble in a wide range of organic solvents and water. Furthermore, reactive functionalities can be introduced with ease into PEG macromolecules, making it an excellent candidate for the functionalization of biologically important materials.

Herein, materials possess "stealth properties" if they exhibit low propensity to interact with biological materials (e.g., opsonins) of the physiological environment (e.g., blood stream). When PEG is present in the blood stream, a protective sheath of hydrogen bonded water molecules surrounds the PEG chains. The hydrated PEG chains can exhibit excellent stealth properties. For example, PEG-stabilized drug compositions have been characterized as having reduced enzymatic degradation, decreased uptake by the reticular endothelial system, and reduced renal filtration, which in turn lead to increased blood circulation half-life and bioavailability. Attaching PEG to a therapeutically useful material (e.g., drug) can also significantly decrease the toxicity of the material.

Herein, the term "PEGylated" means comprising a PEG polymer chain. The PEG can be bound covalently and/or non-covalently. PEGylated products have been on the market for approximately 20 years.

A drawback of PEG is its non-biodegradability. The molecular weight necessary for renal clearance is difficult to determine. Generally, PEG that has a number average molecular weight below about 20 kDa can be excreted into urine. PEG that has a number average molecular weight (Mn) above 40-60 kDa is prone to accumulate in the liver. Higher molecular weight PEG can also accumulate at other body sites by mechanisms that remain unknown. PEG accumulation is not a high concern when used short term, but for repeated administration such as with chronic disease treatment, the use of high molecular weight PEG is a concern. PEG having a number average molecular weight (Mn) of about 40 kDa is commonly used for PEGylation of biologically active molecules.

In addition to PEG being non-biodegradable, the side products (e.g. 1,4-dioxane) formed during PEG synthesis and the residual unreacted ethylene oxide monomer are toxic. These byproducts are known carcinogens and are regulated for pharmaceutical grade PEG.

Immunological responses have also been associated with PEG. Although PEG is a stealth polymer, in some formulations PEG induces an immune response when administered intravenously, orally, and/or dermally.

The disadvantages associated with PEG provide motivation to develop alternative polymers for therapeutic delivery of therapeutic agents (e.g., hydrophobic drugs). Although significant research has been performed in this area, there are few synthetic alternatives offering the same stealth properties that can be prepared with the same level of synthetic control. A desirable PEG replacement would biodegrade into non-toxic byproducts. Scheme 1 shows examples of some current biodegradable PEG replacements based on poly(amino acids), where each subscript m is independently a number having an average value greater than 1. Of the three polymers shown, only poly(L-glutamic acid) is approved by the U.S. Food and Drug Administration (FDA).

Scheme 1.

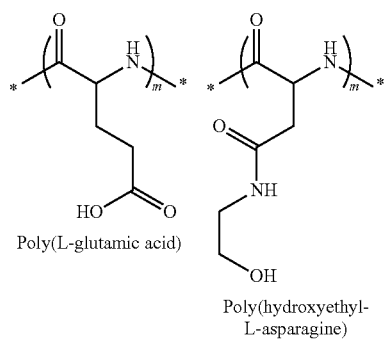

Poly(L-glutamic acid)

Poly(hydroxyethyl-L-asparagine)

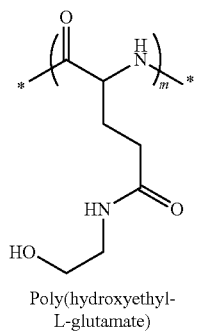

Poly(hydroxyethyl-L-glutamate)

Other non-biodegradable polymers are also of interest as PEG alternatives (Scheme 2, where each subscript m is independently a number having an average value greater than 1). Many of these polymers are promising as PEG alternatives for applications where only low molecular weight polymers are needed. At high molecular weights, bioaccumulation can become problematic. Poly(N-(2-hydroxypropyl) methacrylamide) and poly(glycerol) have reached clinical trials.

Scheme 2.

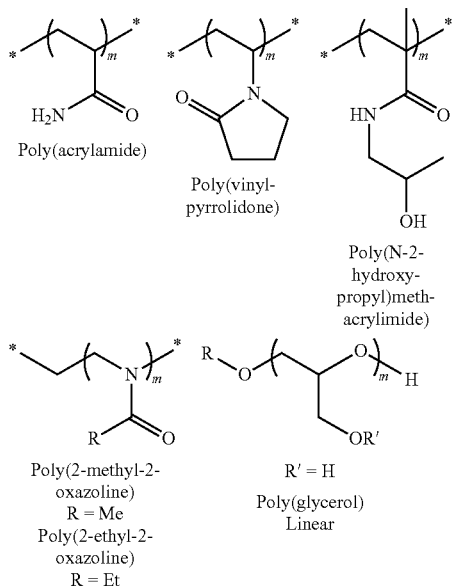

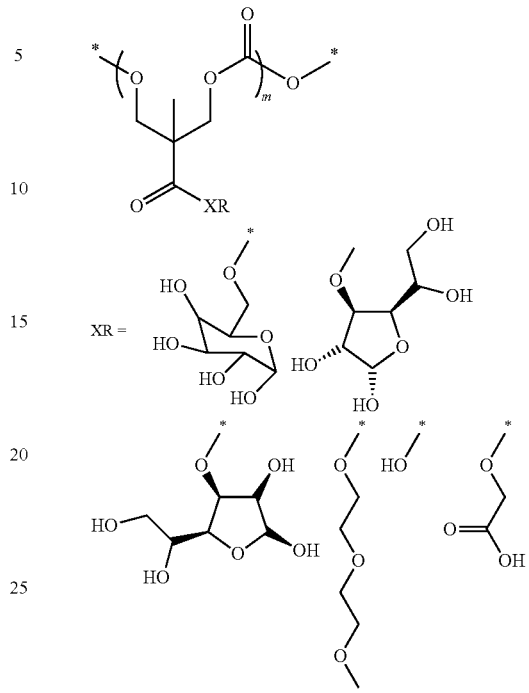

Scheme 3.

A few biodegradable water soluble polycarbonates have been prepared as alternatives to PEG. These are shown in Scheme 3, where in each case subscript m is independently a number having an average value greater than 1.

The sugar-containing polymers are limited because receptors of the body can bind to sugars. For example, galactose can be used to target liver cells. The polycarbonates containing the short PEG side groups can be used as an alternative to PEG; however, these are synthetically challenging to work with because of ring chain equilibrium. The bulkier the side chain, the more difficult it is to obtain a high degree of polymerization. The remaining polycarbonates are negative-charged, which limits their solubility in organic solvents.

Therefore, a need continues for hydrophilic polymers suitable for delivery of therapeutic agents for medical treatments. The hydrophilic polymers should be biodegradable, non-toxic, and soluble in organic solvents and water. The hydrophilic polymers should not induce an undesirable immune response. The hydrophilic polymers should be accessible in a range of molecular weights having narrow PDIs, and should degrade to non-toxic byproducts.

SUMMARY

Accordingly, a polymer is disclosed that comprises a carbonate repeat unit of formula (1):

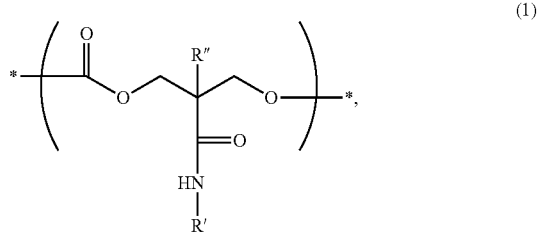

wherein

R' is a monovalent radical comprising 2 to 4 carbons and 1 to 2 hydroxy groups,

R" is a monovalent radical selected from the group consisting of hydrogen, methyl, ethyl, and propyl, the polymer is non-charged, and the polymer is soluble in water.

Also disclosed is a composition, comprising:

an above-described polymer; and a therapeutic agent for a medical treatment, the therapeutic agent selected from the group consisting of genes, proteins, peptides, drugs, and combinations thereof;

wherein the polymer and the therapeutic agent are bound by non-covalent interactions, the composition is dispersible in water as a particle having an average circular diameter of about 10 nm to about 500 nm, and an aqueous mixture of the composition is suitable for intravenous injection.

Also disclosed is a method, comprising:

forming a first mixture comprising water and a polymer comprising a carbonate first repeat unit of formula (1):

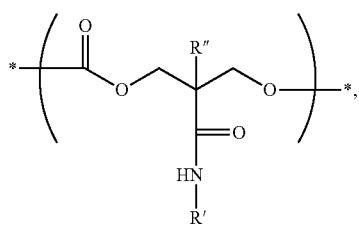

(1)

wherein i) R' is monovalent radical comprising 2 to 4 carbons and 1 to 2 hydroxy groups, ii) R" is selected from the group consisting of hydrogen, methyl, ethyl, and propyl, and iii) the polymer is soluble in the water;

forming a second mixture comprising i) a solvent selected from the group consisting of organic solvents, water, and combinations thereof and ii) a therapeutic agent for a medical treatment, the therapeutic agent selected from the group consisting of genes, proteins, peptides, drugs, and combinations thereof;

combining the first mixture and the second mixture, thereby forming a third mixture; and removing organic solvent from the third mixture, thereby forming a particle comprising the polymer and the therapeutic agent bound by non-covalent interactions, wherein the particle is dispersible in water, and an aqueous mixture of the particle is suitable for intravenous injection.

The above-described and other features and advantages of the present invention will be appreciated and understood by those skilled in the art from the following detailed description, drawings, and appended claims.

DETAILED DESCRIPTION

Figure 1:
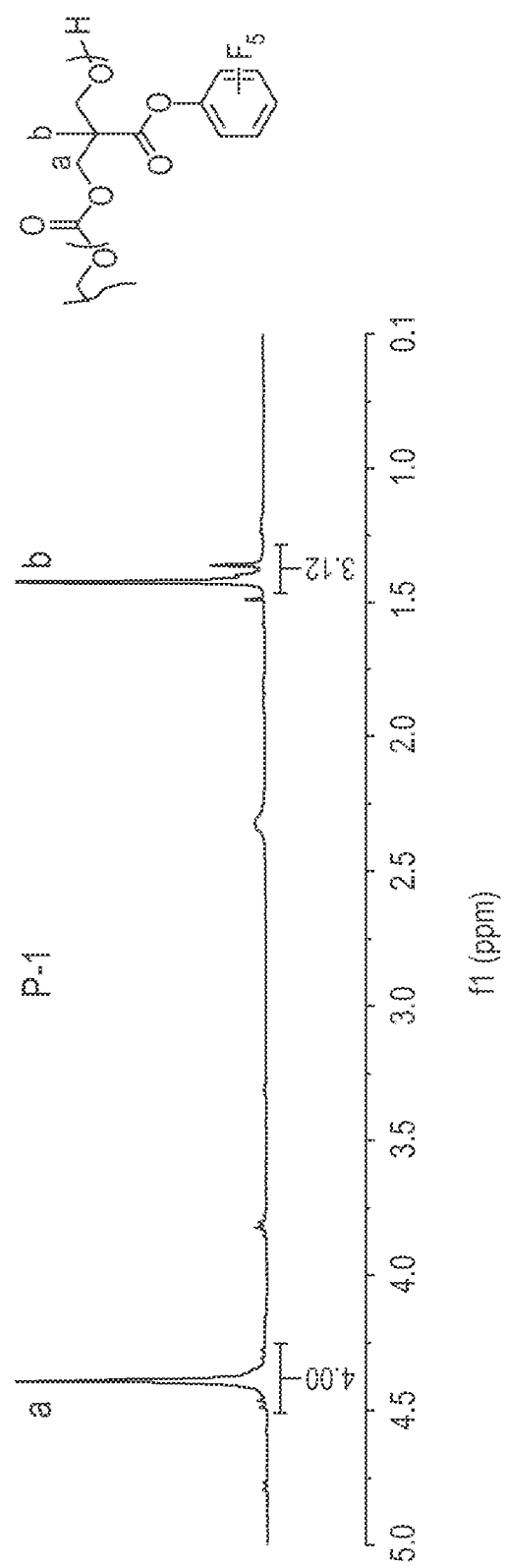
FIG. 1 is a $^1$H NMR spectrum of P-1 formed in Example 1.

The disclosed hydrophilic polymers comprise a carbonate repeat unit of formula (1):

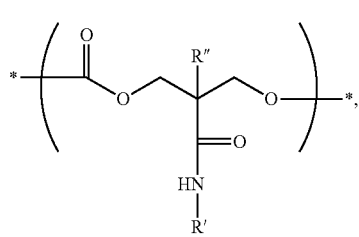

(1)

wherein

R' is a monovalent radical comprising 2 to 4 carbons and 1 to 2 hydroxy groups, and R" is a monovalent radical selected from the group consisting of hydrogen, methyl, ethyl, and propyl.

Herein, a starred bond represents an attachment point, not a methyl group.

The hydrophilic polymers can consist essentially of non-charged repeat units. The hydrophilic polymers preferably induce little or no flocculation of a serum solution over a 48 hour period. A phosphate buffered serum mixture containing a hydrophilic polymer can have an average particle size (based on an average circular diameter determined by dynamic light scattering) in a range of about 10 nm to about 500 nm, more specifically about 10 nm to about 150 nm, and even more specifically about 10 nm to about 60 nm after 48 hours compared to the initial serum mixture.

The hydrophilic polymers can comprise one or two polymer branches. Each polymer branch can comprise a polycarbonate backbone (i.e., composed of carbonate repeat units) or a polyestercarbonate backbone (i.e., composed of ester repeat units and carbonate repeat units). Each polymer branch can be a homopolymer, a random copolymer, or a block copolymer comprising the carbonate repeat unit of formula (1).

More specific hydrophilic homopolymers have a structure according to formula (1a):

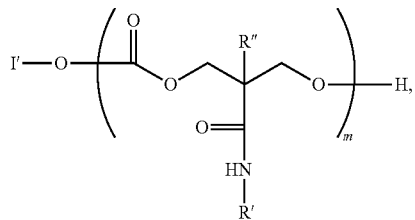

wherein m is a number having an average value greater than 1,

I' is a monovalent radical comprising 1 to 20 carbons, each R" is an independent monovalent radical selected from the group consisting of hydrogen, methyl, ethyl, and propyl, and each R' is an independent monovalent radical selected from the group consisting of:

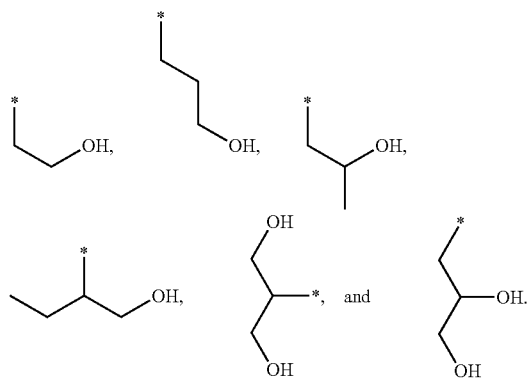

The hydrophilic polymer of formula (1a) comprises one polymer branch emanating from a polymer chain end group I'—O—*, and the polymer branch is a homopolymer of the carbonate repeat units shown. In an embodiment, the fragment I'—O—* is a residue of a monol initiator for the ring opening polymerization (ROP) used to prepare the hydrophilic polymer.

More specific hydrophilic random copolymers have a structure according to formula (2):

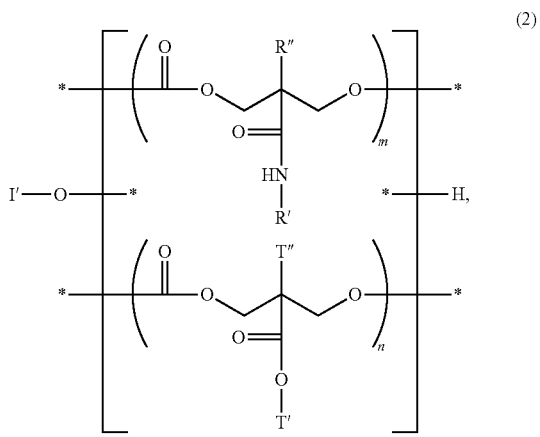

wherein m is a number having an average value greater than 1, n is a number having an average value greater than 1, each T' is an independent monovalent radical comprising 1 to 6 carbons, each T" is an independent monovalent radical independently selected from the group consisting of alkyl groups comprising 1 to 30 carbons and aryl groups comprising 6 to 30 carbons, each R" is an independent monovalent radical selected from the group consisting of hydrogen, methyl, ethyl, and propyl, I' is a monovalent group comprising 1 to 20 carbons, and each R' is selected from the group consisting of:

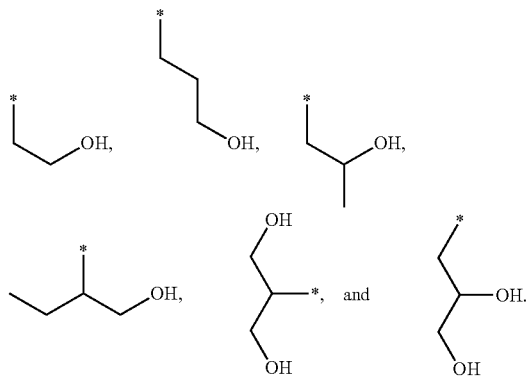

The vertical stacking of the repeat units within the square brackets indicates random distribution of the two carbonate repeat units shown. The first carbonate repeat unit is of formula (1) having a hydrophilic amide side chain *—(C=O)—NH—R'. The second carbonate repeat unit has a non-charged hydrophobic ester side chain *—(C=O)—O-T'. In this instance, the hydrophilic polymer comprises one polymer branch emanating from a polymer chain end group I'—O—*, and the polymer branch is a random copolymer of the two repeat units shown. Either repeat unit of formula (3) can be linked to the end group I'—O—*, and either repeat unit can be a terminal repeat unit at the opposing end of the polymer chain. In this instance, the polymer chain comprises a terminal hydroxy group capable of initiating a ROP. Subscripts m and n represent the average numbers of the respective repeat units in the copolymer chain.

More specific hydrophilic diblock polymers have a structure according to formula (3):

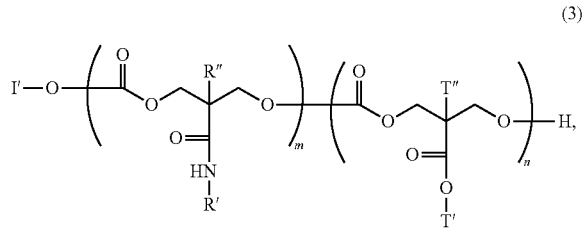

(3)

wherein m is a number having an average value greater than 1, n is a number having an average value greater than 1, I' is a monovalent radical comprising 1 to 20 carbons, each R" is an independent monovalent radical selected from the group consisting of hydrogen, methyl, ethyl, and propyl, each T" is an independent monovalent radical selected from the group consisting of hydrogen, methyl, ethyl, and propyl, each T' is an independent monovalent radical selected from the group consisting of alkyl groups comprising 1 to 30 carbons and aryl groups comprising 6 to 30 carbons, and each R' is an independent monovalent radical selected from the group consisting of:

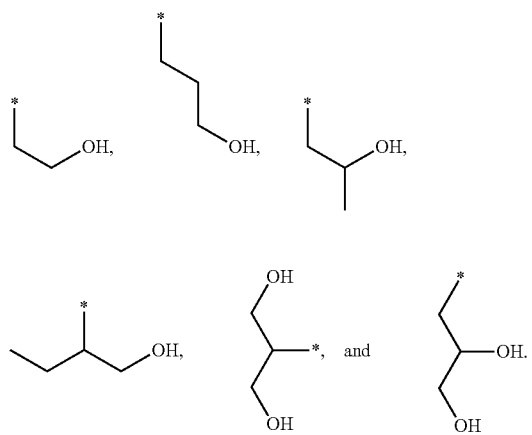

The hydrophilic polymer of formula (3) comprises one polymer branch emanating from a polymer chain end group I'—O—*, and the polymer branch is a diblock copolymer of the two carbonate repeat units shown. The first carbonate repeat unit is of formula (1) having a hydrophilic amide side chain *—(C═O)—NH—R'. The second carbonate repeat unit has a non-charged hydrophobic ester side chain *—(C═O)—O-T'. A first block comprises a homopolymer of the first carbonate repeat unit, and a second block comprises a homopolymer of the second carbonate repeat unit. In an embodiment, the fragment I'—O—* is a residue of a monol initiator for a ring opening polymerization (ROP) used to prepare the hydrophilic polymer.

Other more specific hydrophilic polymers have two polymer branches, wherein each of the polymer branches is linked to a divalent linking group *—O—I"—O—*, as in structures of formula (4):

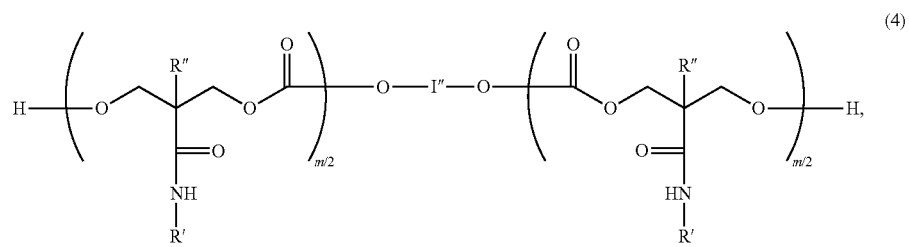

(4)

wherein m is a number having an average value greater than 1,

I" is a divalent linking group comprising 2 to 20 carbons, each R" is an independent monovalent radical selected from the group consisting of hydrogen, methyl, ethyl, and propyl, and each R' is an independent monovalent radical selected from the group consisting of

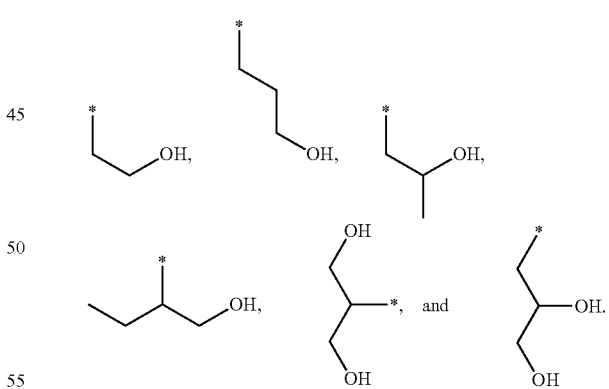

The hydrophilic polymer of formula (4) comprises 2 polymer branches emanating from a central fragment *—O—I"—O—*, and each of the polymer branches is a homopolymer of the carbonate repeat unit of formula (1). In an embodiment, the fragment *—O—I"—O—* is a residue of a diol initiator for a ring opening polymerization (ROP) used to prepare the hydrophilic polymer. In another embodiment, m has an average value of about 10 to about 100. In another embodiment, the side chain *—C═O(NH—R) is an amide of 2-amino-1,3-propanediol (serinol), wherein R' is:

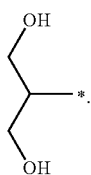

Preferably, in the above structures m has an average value of about 10 to about 100 and n, when present, has an average value of about 0.20 m to about 0.4 m.

In some instances, the hydrophilic polymers exhibit no critical micelle concentration (CMC) below 500 mg/L in water.

The hydrophilic polymers can be biodegradable and/or biocompatible. The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

Herein, "restricted metals" include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the hydrophilic polymer of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the hydrophilic polymer (i.e., the concentration is below detection limits). In an embodiment, the chemical formulas of the components used in the ring opening polymerization (ROP), including the cyclic monomers, the ROP initiator, the catalyst for the ring opening polymerization, the solvent, and any base accelerator, contain none of the above restricted metals. The therapeutic agent can comprise a restricted metal.

No restriction is placed on the concentration of boron, silicon, or any individual alkali metal in the disclosed polymer and/or compositions thereof The hydrophilic polymers can be non-toxic. Preferably, the polymers exhibit an intravenous LD50 value of 500 mg/kg or more. Herein, intravenous LD50 of a substance refers to the median lethal intravenous dosage in milligrams of the substance per kilogram of a test mammal's (e.g., mouse) body mass that kills 50% of the test mammal population in a specified time period.

Methods of Forming Hydrophilic Polymers

In the following description, the term "cyclic carbonyl monomer" includes cyclic carbonate monomers, cyclic ester monomers, and combinations thereof that can be polymerized in a ring opening polymerization.

The hydrophilic polymers are preferably formed by an organocatalyzed ring-opening polymerization (ROP). Two or more ROPs can be conducted sequentially to form block copolymers.

The ROP reaction mixture includes a first cyclic carbonate monomer that has a pendant active ester side chain. Non-limiting exemplary active esters include pentafluorophenyl ester (PFP), pentachlorophenyl ester, para-nitrophenyl ester, and N-hydroxysuccinimidyl ester. Preferably, the first cyclic carbonate monomer comprises a pendant pentafluorophenyl ester (PFP) group. The ROP reaction forms a living initial polymer containing a plurality of repeat units that comprise a pendant active ester group. The initial polymer has a living end group (hydroxy group) capable of initiating another ROP, which can optionally be end capped. Treatment of the initial polymer or the endcapped initial polymer with an amino-alcohol compound produces the disclosed hydrophilic polymer comprising the carbonate repeat unit of formula (1). The active ester preferably selectively reacts with the amine group of the amino-alcohol without causing significant aminolysis of the initial polymer backbone.

A non-limiting example of a first cyclic carbonate monomer comprising an active ester group is MTC-C6F5, which has a pendant pentafluorophenyl ester (PFP) group.

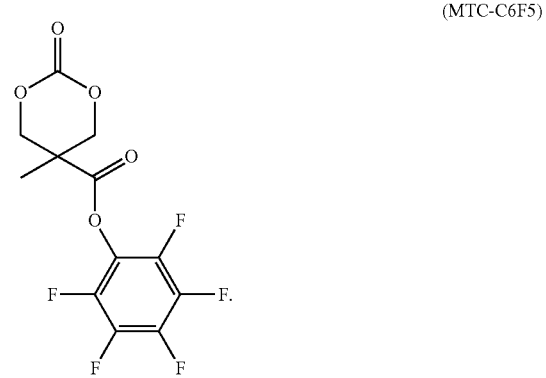 [SMILES: CC1(C(=O)Oc2c(F)c(F)c(F)c(F)c2F)COC(=O)OC1]

(MTC-C6F5)

Cyclic carbonate monomers comprising active ester side chains can be used singularly or in combination.

ROP Catalyst

The ROP reaction mixture includes an organocatalyst whose chemical structure preferably contains none of the restricted metals described further above.

The organocatalyst is preferably an organic acid. Exemplary organic acids include diphenylphosphate, sulfuric acid, p-toluenesulfonic acid, methanesulfonic acid, and trifluoromethane sulfonic acid (triflic acid). In an embodiment, the organocatalyst is trifluoromethane sulfonic acid.

Other organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

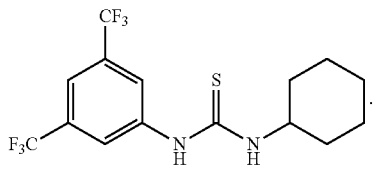
(TU)

Other ROP organocatalysts comprise at least one 1,1,1,3,3,3-hexafluoropropan-2-ol-2-yl (HFP) group. Singly-donating hydrogen bond catalysts have the formula (5):

$$R^2\text{—}C(CF_3)_2OH \qquad (5),$$

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 1.

TABLE 1

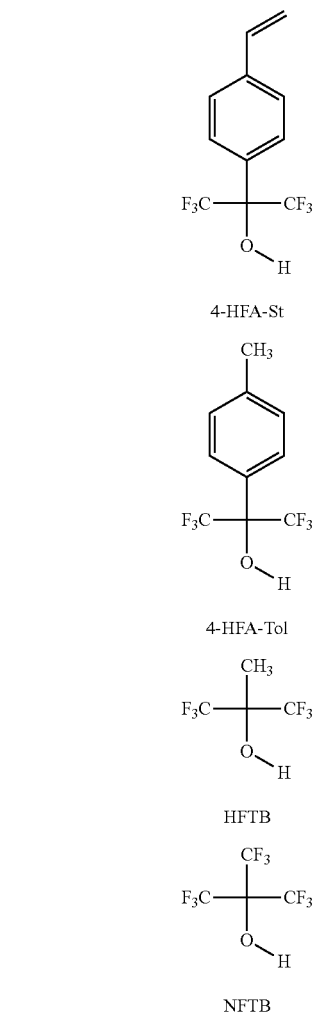

TABLE 1-continued

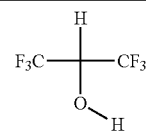

HFIP

Doubly-donating hydrogen bonding catalysts have two HFP groups, represented by the formula (6):

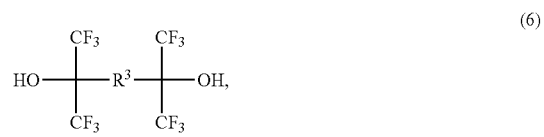
(6)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (6) include those listed in Table 2. In a specific embodiment, $R^2$ is an arylene or substituted arylene group, and the HFP groups occupy positions meta to each other on the aromatic ring.

TABLE 2

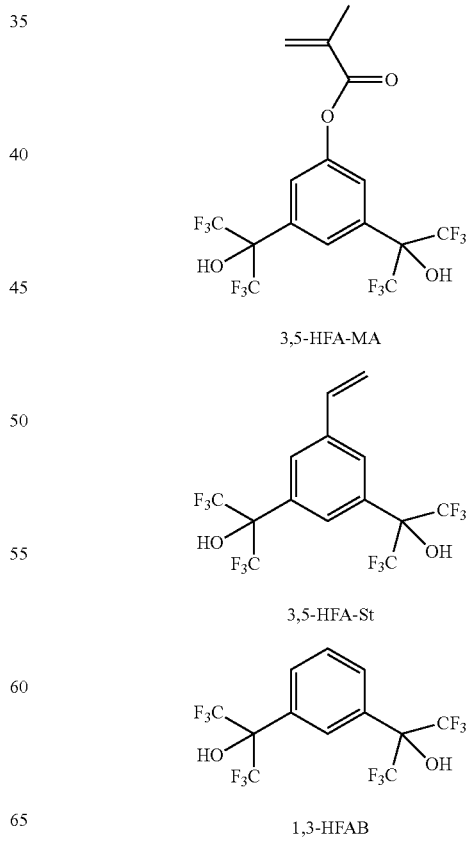

TABLE 2-continued

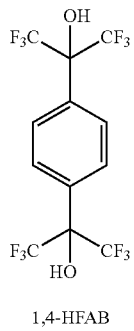

1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst can be added in a proportion of 1/20 to 1/40,000 moles relative to the cyclic carbonyl monomers, and preferably in a proportion of 1/1,000 to 1/20,000 moles relative to the cyclic carbonyl monomers.

ROP Initiators

The ROP reaction mixture includes an initiator. The ROP initiator can have 1 or more nucleophilic groups selected from the group consisting of alcohols, amines, thiols, and combinations thereof. Most preferably the ROP initiator is a monol and/or diol initiator comprising 1 to 20 carbons. The initiator can include other functional groups such as, for example, a halide, ester, amide, ether, urea, and/or protected nucleophilic groups such as protected thiols, protected amines, and protected alcohols.

Exemplary mono-nucleophilic initiators include mono-alcohols, such as methanol, ethanol, propanol, propargyl alcohol, butanol, 3-butyn-1-ol, 2-hydroxyethyl acrylate, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol, pyrene butanol, and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohols, and the like.

Exemplary dinucleophilic initiators include benzenedimethanol, hydroquinone, resorcinol, propylene glycol, ethylene glycol, diethylene glycol, and triethylene glycol, 1,3-propanediol, 1,4-butanediol, 1,5-pentanediol, and 1,6-hexanediol. An even more specific dinucleophilic initiator is BnMPA, a precursor used in the preparation of cyclic carbonate monomers:

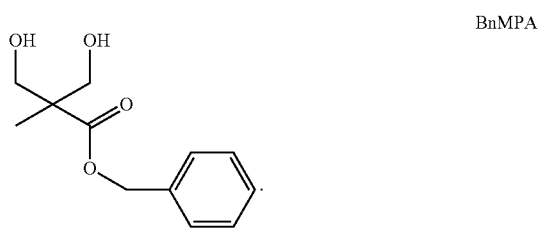 [SMILES: CC(CO)(CO)C(=O)OCc1ccccc1]

BnMPA

When prepared with a monol initiator, the initiator becomes the fragment I'—O—*, as in formula (2) shown further above. When prepared with a diol initiator, the initiator becomes the fragment *—O—I'—O—*, as in formula (3) shown further above.

Diluent Monomers

The ROP reaction mixture can include a second hydrophobic cyclic carbonyl monomer selected from the group consisting of cyclic carbonates, cyclic esters, and combinations thereof, which can undergo ring opening to form a hydrophobic carbonate and/or ester second repeat unit, respectively. The second repeat units can act as diluents for adjusting the hydrophilic/hydrophobic balance of the hydrophilic polymers. That is, the amphiphilic properties of the hydrophilic polymers can be controlled by adjusting the amount and structure of the first cyclic carbonate monomer and/or the amount and structure of a diluent second cyclic carbonyl monomer.

More specific diluent cyclic carbonate monomers have a structure according to formula (7):

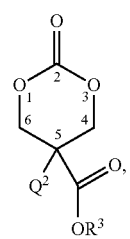

(7)

wherein each $Q^2$ is a monovalent radical independently selected from the group consisting of hydrogen and alkyl groups comprising 1 to 5 carbons, and $R^3$ is a monovalent radical independently selected from the group consisting of alkyl groups comprising 1 to 30 carbons and aryl groups comprising 6 to 30 carbons.

The second repeat unit formed by ring opening polymerization of the diluent monomer of formula (7) has the formula (8):

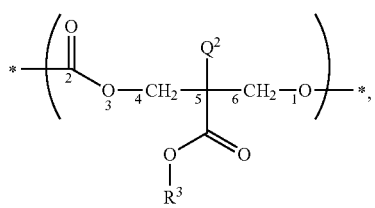

(8)

wherein $Q^2$ and $R^3$ are defined as above, and backbone carbons and oxygens are numbered as shown. This second repeat unit comprises a backbone carbonate group. In an embodiment, $R^3$ is a group comprising 1 to 6 carbons, and $Q^2$ is methyl or ethyl.

Other more specific examples of diluent cyclic carbonate monomers are listed in Table 3.

TABLE 3

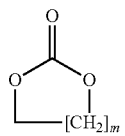

m = 1: Trimethylene carbonate (TMC)
m = 2: Tetramethylene carbonate (TEMC)
m = 3: Pentamethylene carbonate (PMC)

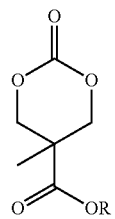

R = methyl (MTCOMe)
R = t-butyl (MTCO$^t$Bu)
R = ethyl (MTCOEt)

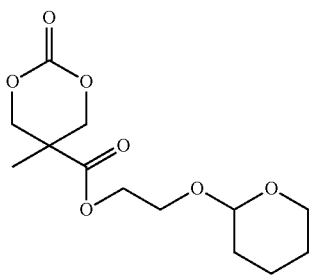 [SMILES: CC1(C(=O)OCCOC2CCCCO2)COC(=O)OC1]

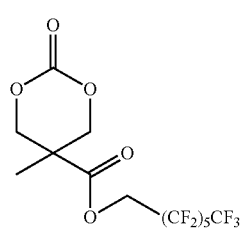

TABLE 3-continued

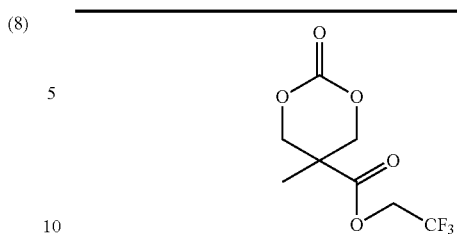

(MTCTFE)

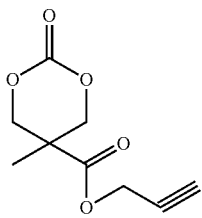

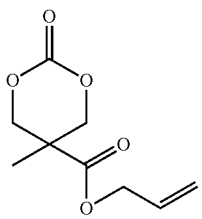

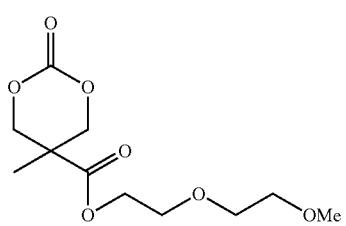 [SMILES: COCCOCCOC(=O)C1(C)COC(=O)OC1]

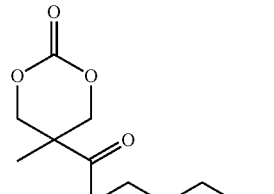

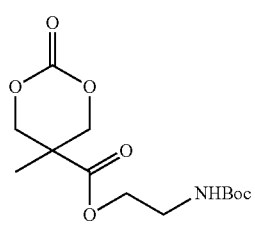 [SMILES: CC(C)(C)OC(=O)NCCOC(=O)C1(C)COC(=O)OC1]

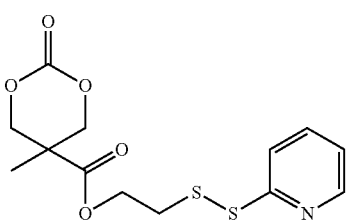 [SMILES: CC1(C(=O)OCCSSc2ccccn2)COC(=O)OC1]

TABLE 3-continued
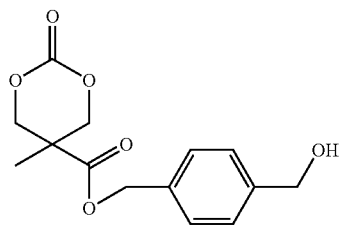 [SMILES: CC1(C(=O)OCc2ccc(CO)cc2)COC(=O)OC1]
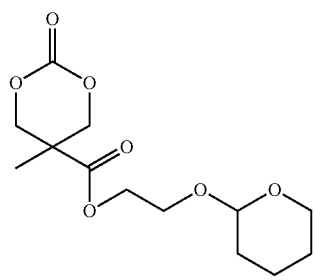 [SMILES: CC1(C(=O)OCCOC2CCCCO2)COC(=O)OC1]
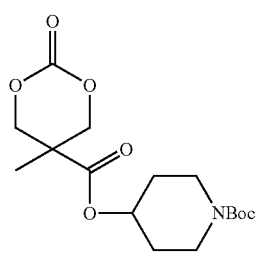 [SMILES: CC(C)(C)OC(=O)N1CCC(OC(=O)C2(C)COC(=O)OC2)CC1]
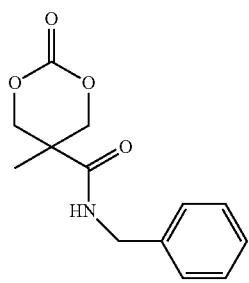 [SMILES: CC1(C(=O)NCc2ccccc2)COC(=O)OC1]
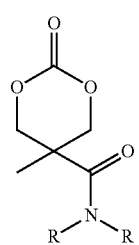
R = methyl
R = iso-propyl
TABLE 3-continued
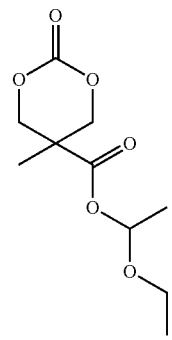 [SMILES: CCOC(C)OC(=O)C1(C)COC(=O)OC1]
(MTCOEE)
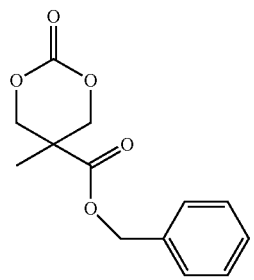 [SMILES: CC1(C(=O)OCc2ccccc2)COC(=O)OC1]
(MTCOBn)
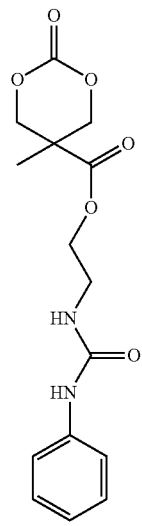 [SMILES: CC1(C(=O)OCCNC(=O)Nc2ccccc2)COC(=O)OC1]
MTCU
Exemplary cyclic ester monomers (e.g., lactones) include compounds of the formula (9):
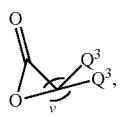
(9)
wherein v is an integer of 1 to 8, each $Q^3$ is a monovalent radical independently selected from the group consisting of hydrogen, alkyl groups comprising 1 to 30 carbons, and aryl groups comprising 6 to 30 carbon atoms. The cyclic ester ring can optionally comprise a carbon-carbon double bond; that is, optionally, a

group of formula (9) can independently represent a

group. The cyclic ester ring can also comprise a heteroatom such as oxygen, nitrogen, sulfur, or a combination thereof; that is, optionally a

group of formula (9) can independently represent a *—O—*, *—S—*, *—N(H)—*, or an *—N($R^1$)—* group, wherein $R^1$ is a monovalent radical independently selected from the group consisting of alkyl groups comprising 1 to 30 carbons and aryl groups comprising 6 to 30 carbons. Cyclic ester monomers of formula (9) can be stereospecific or non-stereospecific.

The second repeat unit formed by ring opening polymerization of the diluent monomer of formula (9) has the formula (10):

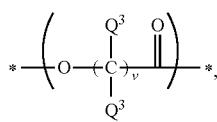
(10)

wherein $Q^3$ and v are defined as above under formula (9). The second repeat unit comprises a backbone ester group.

Other non-limiting examples of diluent cyclic ester monomers include the compounds of Table 4 and stereospecific versions thereof where feasible.

TABLE 4

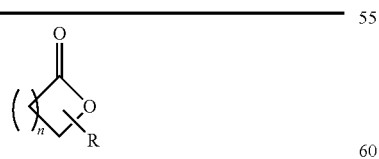

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = $CH_3$; n = 1: beta-Butyrolactone (b-BL)
R = $CH_3$; n = 2: gamma-Valerolactone (g-VL)

TABLE 4-continued

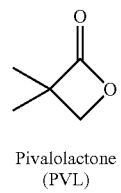

Pivalolactone
(PVL)

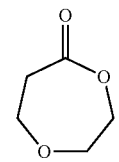

1,5-Dioxepan-2-one
(DXO)

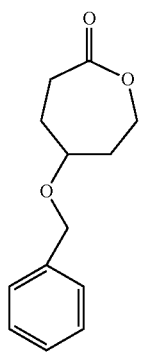 [SMILES: O=C1CCC(OCc2ccccc2)CCO1]

5-(Benzyloxy)oxepan-2-one
(BXO)

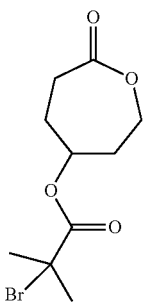

7-Oxooxepan-4-yl 2-bromo-2-methylpropanoate
(BMP-XO)

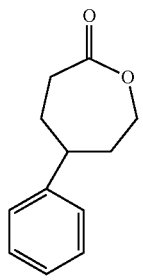 [SMILES: O=C1CCC(c2ccccc2)CCO1]

5-Phenyloxepan-2-one
(PXO)

TABLE 4-continued

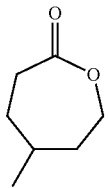

5-Methyloxepan-2-one
(MXO)

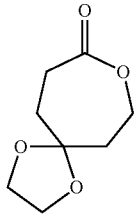

1,4,8-Trioxa(4,6)spiro-9-undecane
(TOSUO)

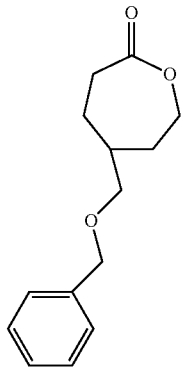 [SMILES: O=C1CCC(COCc2ccccc2)CCO1]

5-(Benzyloxymethyl)oxepan-2-one (BOMXO)

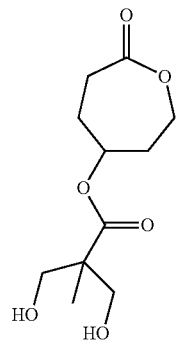 [SMILES: CC(CO)(CO)C(=O)OC1CCOC(=O)CC1]

7-Oxooxepan-4-yl 3-hydroxy-2-
(hydroxymethyl)-2-methylpropanoate
(OX-BHMP)

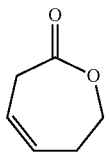

(Z)-6,7-Dihydrooxepin-2(3H)-one (DHXO)

Other diluent cyclic ester monomers are dioxane dicarbonyl monomers of formula (11):

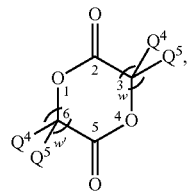

(11)

wherein w and w' are independent integers having a value of 1 to 3, and each $Q^4$ and each $Q^5$ is a monovalent radical independently selected from the group consisting of hydrogen, alkyl groups comprising 1 to 30 carbons, and aryl groups comprising 6 to 30 carbon atoms. Compounds of formula (11) can be stereospecific or non-stereospecific. In an embodiment, w and w' are each 1, each $Q^4$ is hydrogen, and each $Q^5$ is an alkyl group comprising 1 to 6 carbons. In another embodiment, the diluent monomer is D-lactide or L-lactide.

The second repeat unit formed by ring opening polymerization of the diluent monomer of formula (11) has the formula (12):

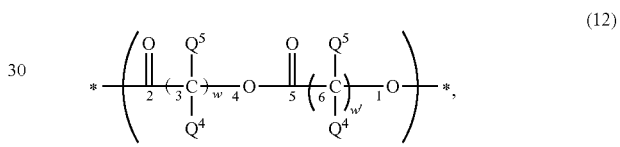

(12)

wherein $Q^4$, $Q^5$, w, and w' are defined as above under formula (11), and backbone carbons and oxygens are numbered as shown. This second repeat unit has two backbone ester groups.

Examples of diluent monomers of formula (11) include the compounds of Table 5.

TABLE 5

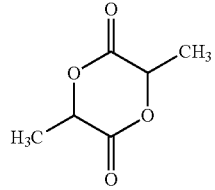

D-Lactide (DLA),
L-Lactide (LLA), or
racemic Lactide, 1:1 D:L forms (DLLA)

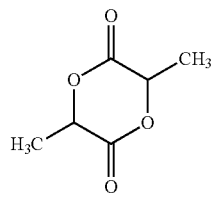

meso-Lactide (MLA)
(two opposite centers of asymmetry,
R and S)

TABLE 5-continued

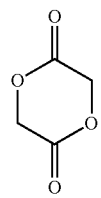

Glycolide (GLY)

The above cyclic carbonyl monomers can be purified by recrystallization from a solvent such as ethyl acetate or by other known methods of purification, with particular attention being paid to removing as much water as possible from the monomer. The monomer moisture content can have a value of 1 to 10,000 ppm, 1 to 1,000 ppm, 1 to 500 ppm, and most specifically 1 to 100 ppm, by weight of the monomer.

The cyclic carbonyl monomers used in the ROP, the first repeat units, and/or the second repeat units can be stereospecific or non-stereospecific. A stereospecific monomer and/or stereospecific repeat unit i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. For example, if a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me2NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 6.

TABLE 6

Pyridine
(Py)

TABLE 6-continued

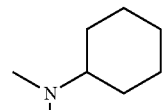

N,N-Dimethylaminocyclohexane
(Me₂NCy)

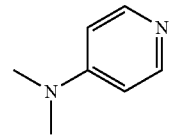

4-N,N-Dimethylaminopyridine
(DMAP)

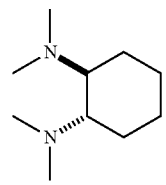

trans 1,2-Bis(dimethylamino)cyclohexane
(TMCHD)

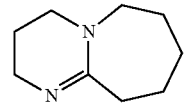

1,8-Diazabicyclo[5.4.0]undec-7-ene
(DBU)

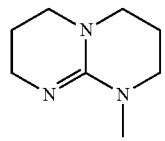

7-Methyl-1,5,7-triazabicyclo[4.4.0]dec-5-ene
(MTBD)

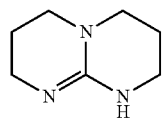

1,5,7-Triazabicyclo[4.4.0]dec-5-ene
(TBD)

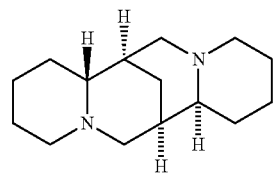 [SMILES: C1CCN2C[C@H]3C[C@H](CN4CCCC[C@@H]34)[C@H]2C1]

(−)-Sparteine
(Sp)

TABLE 6-continued

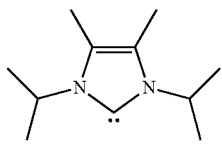

1,3-Bis(2-propyl)-4,5-dimethylimidazol-
2-ylidene
(Im-1)

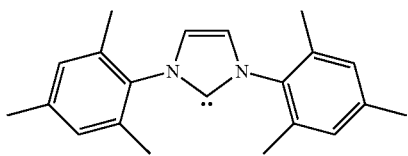

1,3-Bis(2,4,6-trimethylphenyl)imidazol-2-
ylidene
(Im-2)

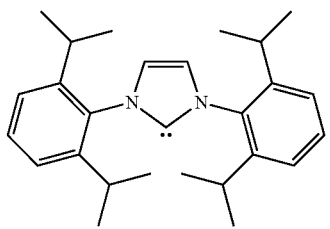

1,3-Bis(2,6-di-i-propylphenyl(imidazol-
2-ylidene
(Im-3)

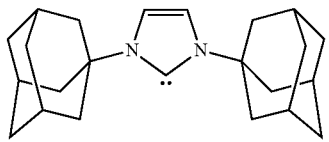

1,3-Bis(1-adamantyl)imidazol-2-yliden)
(Im-4)

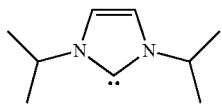

1,3-Di-i-propylimidazol-2-ylidene
(Im-5)

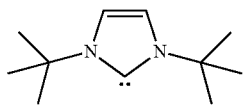

1,3-Di-t-butylimidazol-2-ylidene
(Im-6)

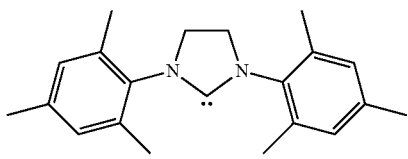

1,3-Bis(2,4,6-trimethylphenyl)-4,5-
dihydroimidazol-2-ylidene
(Im-7)

TABLE 6-continued

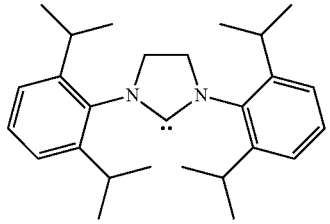

1,3-Bis(2,6-di-i-propylphenyl)-4,5-
dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

ROP Conditions

The ring-opening polymerization is preferably performed at a temperature of about 15° C. to about 50° C., and even more specifically 20° C. to 30° C. Reaction times vary with solvent, temperature, agitation rate, pressure, and equipment. In general, the polymerizations are complete within 1 to 100 hours.

The ROP reaction is preferably performed with a solvent. Exemplary solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted using a dry, inert atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per nucleophilic initiator group. The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of cyclic carbonyl monomer, the amount of initiator is 0.05×50=2.5 g per mole of cyclic carbonyl monomer.

The catalysts can be removed by selective precipitation or in the case of the solid supported catalysts, simply by filtration. The block copolymer can comprise residual catalyst in an amount greater than or equal to 0 wt % (weight percent), based on total weight of the hydrophilic polymer and the residual catalyst.

Amino-Alcohols

The initial polymer formed by the ROP or the endcapped initial polymer is treated with an amino-alcohol, thereby forming a hydrophilic polymer. The amino-alcohol comprises 1 to 4 carbons and 1 or more hydroxyl groups. Particularly preferred amino-alcohols include:

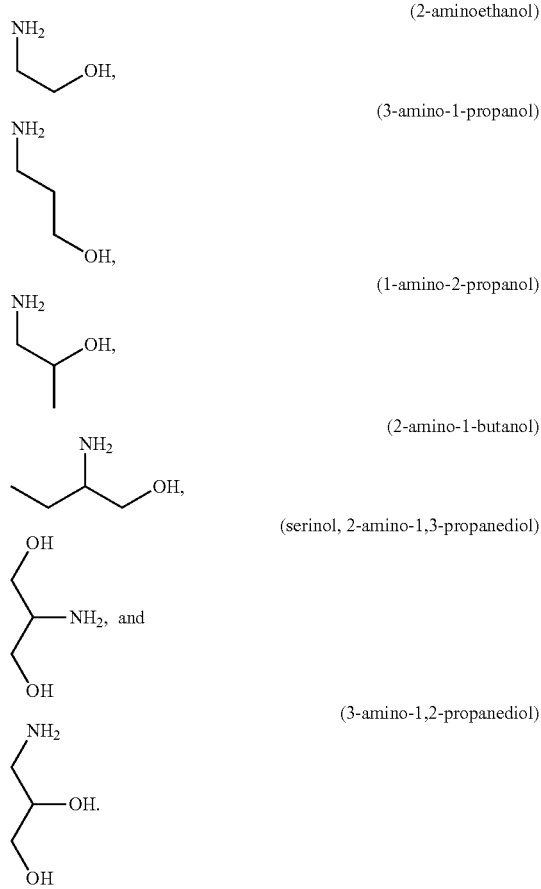

The amino-alcohols can be stereospecific or non-stereospecific. The amino-alcohols can be used singularly or in combination. In an embodiment, the amino-alcohol is serinol (2-amino-1,3-propanediol).

Average Molecular Weight

The hydrophilic polymers preferably have a number average molecular weight Mn of about 1500 or more, more preferably about 1500 to about 50,000, and most preferably about 5000 to about 20,000. In an embodiment, the hydrophilic polymer has a number average molecular weight Mn of about 5000 to about 10,000.

The hydrophilic polymers can have a polydispersity index (PDI) of 1.01 to 2.0, more preferably 1.01 to 1.30, and even more preferably 1.01 to 1.25.

Endcap Agents

The initial polymer and/or the hydrophilic polymer can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap agent can also comprise a biologically active moiety, which becomes bound to the terminal end group of the ring opened polymer chain.

In an embodiment, the hydrophilic polymer has a living end group (i.e., not endcapped), which is capable of initiating a ring opening polymerization.

Cytotoxicity

The hydrophilic polymers alone are generally non-cytotoxic. For example, cell viability of human embryonic kidney cells HEK293 can be in a range of 80% to 100% at polymer concentrations up to 200 mg/L.

Loaded Polymers

Also disclosed are compositions (also referred to herein as "loaded polymers") for a medical treatment comprising a disclosed polymer and a therapeutic agent. The hydrophilic polymer can serve as a carrier for a therapeutic agent, which can be bound to the hydrophilic polymer by non-covalent interactions (e.g., hydrogen bonding, hydrophobic interactions) and/or covalent bonds. The hydrophilic polymer can serve as a dispersing aid for the therapeutic agent in an aqueous mixture.

The compositions can release the therapeutic agent in the blood stream and/or within a cell.

The compositions can be in the form of water-dispersible particles. The particles can have an average particle size as measured by dynamic light scattering of about 10 nm to about 500 nm, more preferably 10 nm to about 200 nm. The particles can further comprise water.

The compositions can comprise the therapeutic agent in an amount greater than 0 weight percent (wt %), and more particularly in an amount of about 0.1 wt. % to about 15 wt % based on total dry weight of the compositions.

The therapeutic agent can be any suitable therapeutic agent capable of forming a reversible complex (i.e., by non-covalent interactions) and/or adduct (i.e., by covalent interactions) with a disclosed hydrophilic polymer, wherein the complex and/or adduct is capable of controlled release of the therapeutic agent. Non-limiting therapeutic agents include DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. In an embodiment, the therapeutic agent is a drug and/or a gene.

The therapeutic agent is effective in inducing a desirable medical response. Non-limiting desirable medical responses include selective alteration of the chemical structure and/or activity of a cell type relative to another cell type. As an example, one desirable change in a chemical structure can be the incorporation of a gene into the DNA of a cell. A desirable change in activity can be the expression of the transfected gene by the cell. Another desirable change in cell activity can be the induced production of a desired hormone or enzyme. Alternatively, a desirable change in activity can be the selective death of one cell type over another cell type.

For example, the therapeutic agent can selectively kill a bacterium, inactivate a virus, and/or kill tumor cells. No limitation is placed on the relative change in cellular activity caused by the therapeutic agent, providing the change is desirable and useful. Moreover, no limitation is placed on the therapeutic agent, providing the therapeutic agent induces a medically useful response.

Non-limiting exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cyclosporin (an immunosuppressive agent, normally given to patients for life long after organ transplantation), Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Finasteride (for hair growth), Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, Spironolactone, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Non-limiting examples of rigid hydrophobic drugs (with stereochemistry shown) include the anti-tumor drug paclitaxel (PTX):

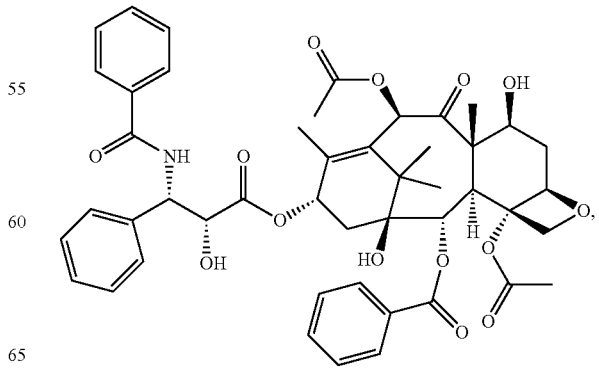

anti-tumor drug doxorubicin (DOX):

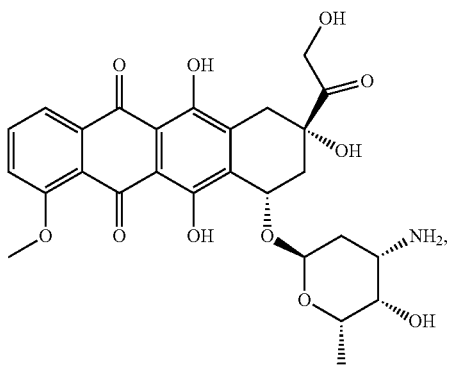 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

immunosuppressive drug cyclosporin A (CYC):

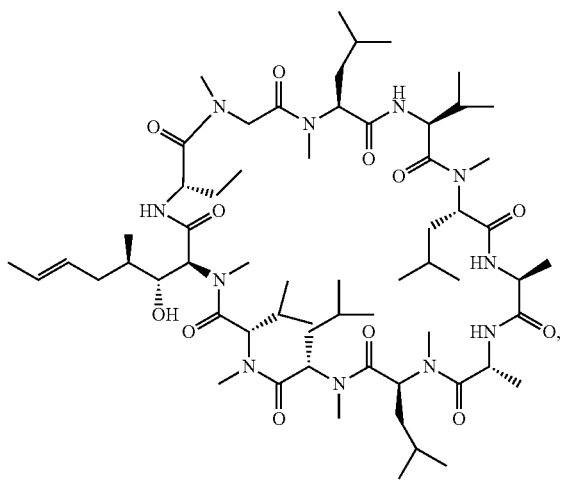 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

and hair growth drug spironolactone (SPL):

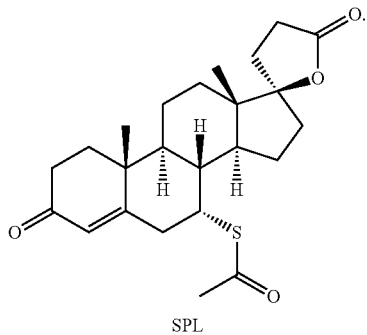

The therapeutic agents can be used singularly or in combination.

Also disclosed is a method of forming a loaded polymer, comprising i) forming a first mixture comprising water and a disclosed hydrophilic polymer, ii) forming a second mixture comprising a therapeutic agent and a solvent selected from the group consisting of organic solvents, water, and combinations thereof, iii) combining the first mixture and the second mixture, thereby forming a third mixture, and iv) removing the organic solvent(s) from the third mixture, thereby forming the loaded polymer as a dispersed particle comprising the hydrophilic polymer and the therapeutic agent bound by non-covalent and/or covalent interactions.

The third mixture can be dialyzed against deionized water using a dialysis membrane system to remove the organic solvent.

Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

The loaded polymer can comprise the hydrophilic polymer in an amount of about 50.0 wt % to about 99.9 wt %, and the therapeutic agent in an amount of about 50.0 wt % to about 0.1 wt %, each based on total dry weight of the loaded polymer.

Particles of the loaded polymer can have an average particle size (circular cross sectional diameter) of 10 nm to 500 nm, more preferably 10 nm to 250 nm, and most preferably 25 nm to 200 nm as measured by dynamic light scattering. For the foregoing particle sizes, the aqueous solution can have a pH of 4.5 to 8.0, more particularly 5.0 to 8.0, or even more particularly 7.0 to 8.0.

Industrial Applicability.

Loaded polymer compositions comprising a disclosed hydrophilic polymer and a therapeutic agent can be used for human and/or non-human medical treatments. The compositions can be administered in the form of a powder, a pill, a liquid solution, paste, and/or a gel. The compositions can be used as a drug. The compositions can be administered topically, orally, as suppositories, and/or by injection, including intravenous injections. The compositions can further comprise water and have the form of a stable aqueous dispersion.

A method comprises contacting a cell with a loaded polymer, thereby killing the cell. In an embodiment, the cell is a microbe. In another embodiment, the cell is a cancer cell.

An antimicrobial composition comprises a loaded polymer comprising a disclosed hydrophilic polymer and an antimicrobial agent. The antimicrobial composition can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the loaded polymer, thereby killing a bacterium. The bacterium can be a Gram-positive bacterium, Gram-negative bacterium, yeast and/or fungus.

The antimicrobial composition can be used in the form of a powder, a pill, and/or an aqueous mixture applied as a freely flowing liquid, spray, cream, injectable mixture, and/or gel. Uses include disinfectants for hands, skin, hair, bone, ear, eye, nose, throat, internal tissue, wounds, and teeth (e.g., as a mouthwash). Still other uses include disinfectants for articles such as medical devices. Medical devices include swabs, catheters, sutures, stents, bedpans, gloves, facial masks, absorbent pads, absorbent garments, internal absorbent devices, and insertable mechanical devices.

The antimicrobial compositions are also attractive for disinfecting surfaces of homes, businesses, and particularly hospitals that contact animal tissue and/or animal fluids. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with the loaded polymer composition, thereby disinfecting the surface. In another embodiment, a method comprises contacting a surface of an article with an aqueous mixture of the composition.

The following examples demonstrate the preparation of the hydrophilic polymers.

EXAMPLES

Materials used in the following examples are listed in Table 7.

TABLE 7

| ABBREVIATION | DESCRIPTION | SUPPLIER |
|---|---|---|
| PEG 10 kDa | Poly(ethylene glycol), Mn 10,000 | Sigma-Aldrich |
| PEG 5 kDa | Poly(ethylene glycol), Mn 5,000 | Sigma-Aldrich |
| PEG 2 kDa | Poly(ethylene glycol), Mn 2,000 | Sigma-Aldrich |
| RPMI-1640 | Roswell Park Memorial Institute medium, bicarbonate buffer, pH 8 | Sigma-Aldrich |
| | 2-Aminoethanol | Sigma-Aldrich |
| | 3-Amino-1-propanol | Sigma-Aldrich |
| | Serinol (2-amino-1,3-propanediol) | Sigma-Aldrich |
| | (±)-3-Amino-1,2-propanediol | Sigma-Aldrich |
| | Propargyl alcohol | Sigma-Aldrich |
| | 1-Amino-2-propanol (racemic) | Sigma-Aldrich |
| | 2-Amino-1-butanol | Sigma-Aldrich |
| FBS | Fetal bovine serum | Invitrogen (USA) |
| PBS | Phosphate buffered saline | 1st BASE (Singapore) |
| | HEK293 cells | ATTC (USA) |
| MTT | 3-(4,5-dimethylthiazol-2-yl)-2,5-diphenyltetrazolium bromide | Sigma-Aldrich |
| DMSO | Dimethylsulfoxide | Sigma-Aldrich |
| Triflic acid | Trifluoromethane sulfonic acid | Sigma-Aldrich |
| TMA | Trimethylamine | Sigma-Aldrich |
| DCM | Dichloromethane | Sigma-Aldrich |
| | 3-Butyn-1-ol | Sigma-Aldrich |

Herein, Mn is the number average molecular weight, Mw is the weight average molecular weight, and MW is the molecular weight of one molecule.

Monomer Synthesis

MTC-C6F5 has the following structure:

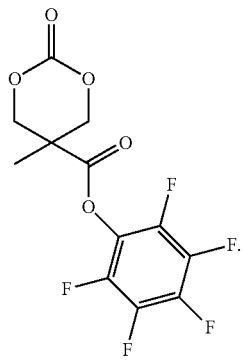 [SMILES: CC1(C(=O)Oc2c(F)c(F)c(F)c(F)c2F)COC(=O)OC1]

MTC-C6F5 was produced using the procedure described by Sanders, et al., "A Simple and Efficient Synthesis of Functionalized Cyclic Carbonate Monomers Using a Versatile Pentafluorophenyl Ester Intermediate", Journal of the American Chemical Society, 2010, 132, pages 14724-14726.

BnMPA has the following structure:

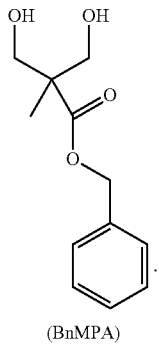 [SMILES: CC(CO)(CO)C(=O)OCc1ccccc1]

(BnMPA)

BnMPA and other cyclic carbonate monomers can be prepared from 2,2-bis(methylol)propionic (BisMPA) according to Scheme 4.

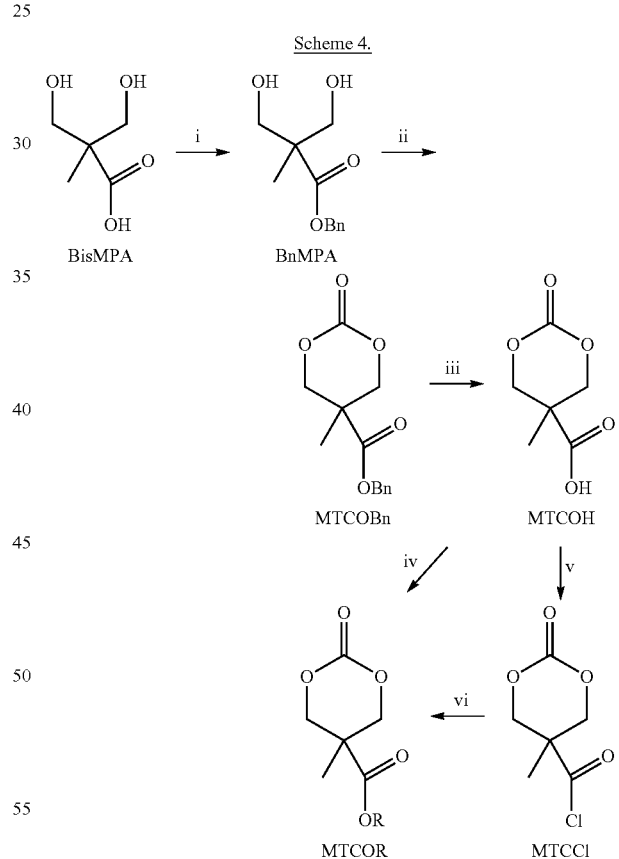

BisMPA can be converted (i) to the benzyl ester BnMPA using known methods. Reaction of BnMPA with triphosgene (ii) produces cyclic carbonyl monomer, MTCOBn. Debenzylation of MTCOBn (iii) produces 5-methyl-5-carboxyl-1,3-dioxan-2-one (MTCOH). Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCC1 followed by treatment (vi) of MTCC1 with ROH in the presence of a base to form MTCOR. Both pathways are illustrative and are not meant to be limiting. The following conditions are typical for the reactions shown in Scheme 4: (i) Benzylbromide (BnBr), KOH, DMF, 100° C., 15 hours, 62% yield of BnMPA; (ii) triphosgene, pyridine, $CH_2Cl_2$, −78° C. to 0° C., 95% yield of MTCOBn; (iii) Pd/C (10%), $H_2$ (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCC1; (vi) ROH, $NEt_3$, room temperature, 3 hours yields MTCOR.

MTCOEt (MW 188.2) has the structure.

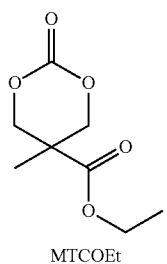

MTCOEt

Using the above Scheme 4, MTCC1 was treated with ethanol to form MTCOEt. MTCOEt was used as a non-functional counterpart for dilution effects and to introduce hydrophobic blocks to the block polymer.

Polymerizations

Example 1

Preparation of Pentafluorophenyl Ester Polymer P-1 Using Diol Initiator BnMPA

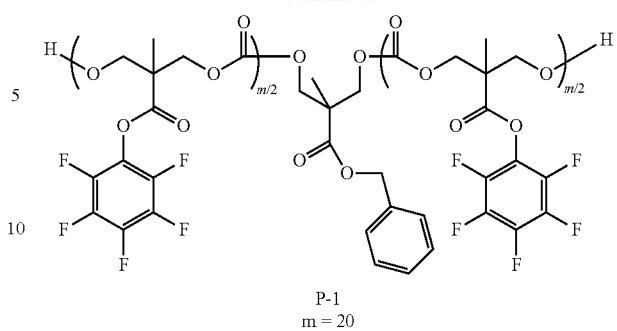

P-1
m = 20

In a nitrogen charged glove box, benzyl 2,2-bis(methylol) propionate initiator (BnMPA, 0.0204 g, 0.91 mmol) and MTC-C6F5 monomer (0.59 g, 1.82 mmol) were dissolved in dichloromethane (12 mL). The catalyst, triflic acid (0.069 g, 0.46 mmol), was added and the reaction mixture was stirred at room temperature overnight. The crude polymer solution was precipitated into hexanes, yielding a white solid. From GPC using THF as eluent, Mn=6200, PDI=1.15, degree of polymerization (DP)=20 (m=20 in the above reaction). FIG. 1 is a $^1H$ NMR spectrum of P-1. The benzyl peak (not shown) of the initiator fragment is in the same region as the $CDCl_3$ peak with these materials. $^1H$ NMR (400 MHz, $CDCl_3$): delta 4.48 (s, 4H, $CH_2$), 1.51 (3H, $CH_3$).

P-1 has two polymer branches emanating from a chain fragment derived from the diol initiator (initiator fragment). Each of the polymer branches consists essentially of a homopolymer chain of repeating units formed by the ROP of MTC-C6F5. A first terminal repeat unit of each homopolymer chain is linked to the initiator fragment. A second terminal repeat unit of each homopolymer chain has a hydroxy group capable of initiating another ROP.

Example 2

Preparation of Diblock Pentafluorophenyl Ester Polymer P-3 from Monol Initiator 3-butyn-1-ol

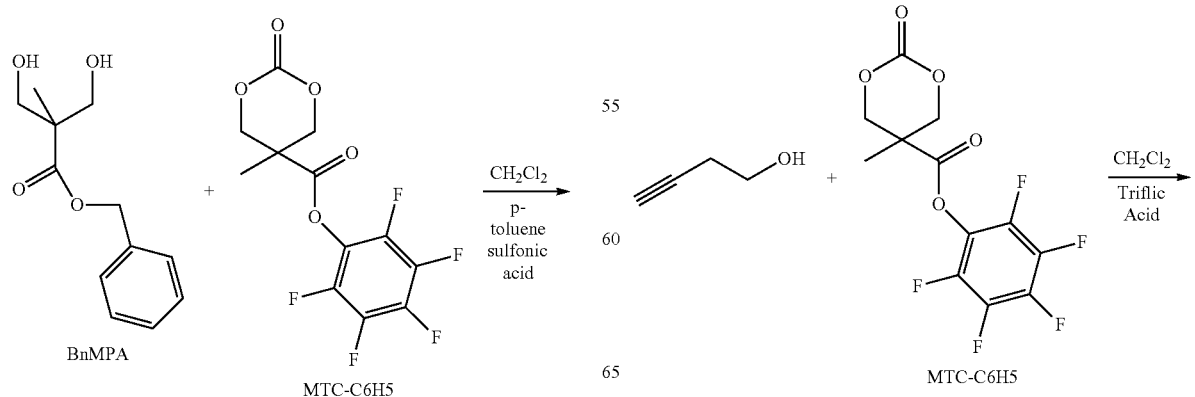

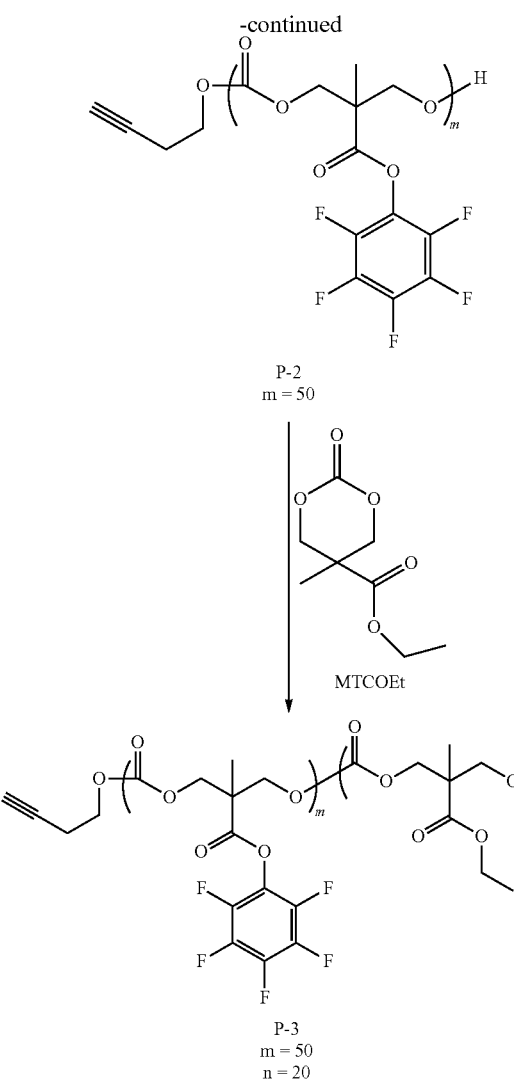

P-2
m = 50

MTCOEt

P-3
m = 50
n = 20

This reaction was performed in a single vessel. In a nitrogen charged glove box, 3-butyn-1-ol initiator (0.085 g, 0.12 mmol) and MTC-C6F5 monomer (1.98 g, 6.06 mmol) were dissolved in dichloromethane (8 mL). The catalyst, triflic acid (0.045 g, 0.30 mmol), was added and the reaction mixture was stirred at room temperature overnight. The reaction conversion was checked by $^1$H-NMR and showed near complete conversion. MTCOEt monomer (0.57 g, 3.03 mmol) was added to the reaction. The reaction was stirred at room temperature and stopped at 73% conversion. The crude polymer was precipitated into hexanes, yielding a white solid P-3. $^1$H NMR (400 MHz, CDCl$_3$): delta 4.48 (s, CH$_2$ poly(MTC-OC$_6$F$_5$), 4H), 4.26 (m, CH$_2$ poly(MTC-OEthyl), 4H), 4.20 (m, CH$_2$CH$_3$ poly(MTC-OEthyl), 2H), 1.51 (s, CH$_3$, 3H) poly(MTC-OC$_6$F$_5$), 1.26 (m, CH$_3$ poly(MTC-OEthyl), 3H), 1.26 (m, CH$_2$CH$_3$ poly(MTC-OEthyl), 3H).

The non-isolated intermediate polymer P-2 has one polymer branch linked to an initiator fragment derived from the monol initiator 3-butyn-1-ol. The polymer branch consists essentially of a homopolymer chain of repeat units formed by the ROP of MTC-C6F5. A first terminal repeat unit of the homopolymer chain is linked to the initiator fragment. A second terminal repeat unit of the homopolymer chain has a hydroxy group capable of initiating another ROP. The initiator fragment is also a polymer branch end group.

The isolated polymer P-3 also has one polymer branch linked to an initiator fragment derived from the monol initiator 3-butyn-1-ol. The initiator fragment is also an end group of the polymer branch. The polymer branch consists essentially of a diblock copolymer chain formed by a first ROP of MTC-C6F5 followed by a second ROP of MTCOEt. The diblock copolymer chain contains a first hydrophilic block derived from MTC-C6F5 and a hydrophobic second block derived from MTCOEt. A first terminal repeat unit of the first block is linked to the initiator fragment. A second terminal repeat unit of the first block is linked to a first terminal repeat unit of second block. A second terminal repeat unit of the second block contains a hydroxy group capable of initiating another ROP.

Example 3

Preparation of Diblock Pentafluorophenyl Ester Polymer P-4

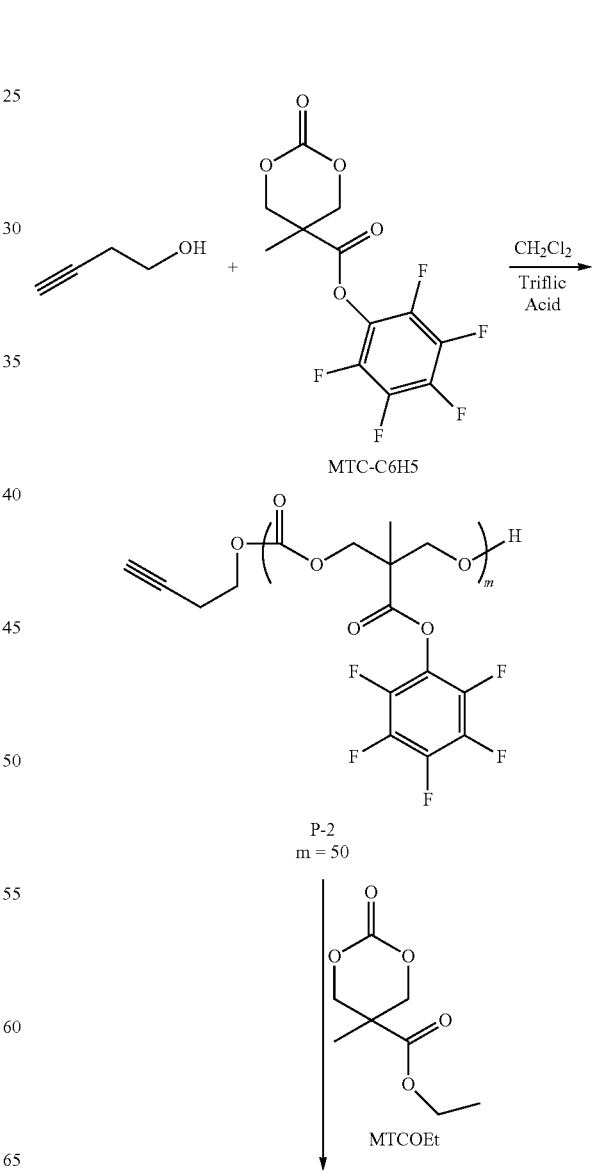

MTC-C6H5

P-2
m = 50

MTCOEt

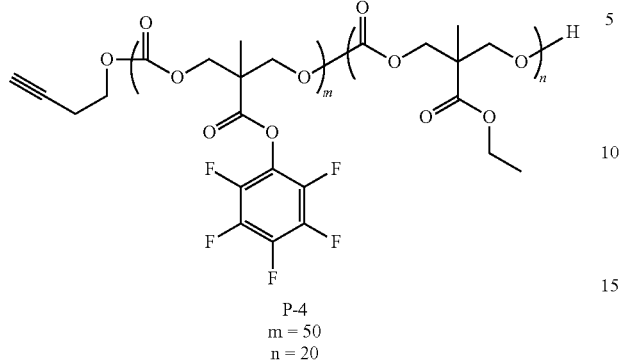

P-4
m = 50
n = 20

P-4 was prepared according to the procedure of Example 2, differing by the size of the block derived from MTCOEt. The amounts used were as follows: 3-butyn-1-ol initiator (0.0085 g, 0.12 mmol) and MTC-C6F5 monomer (1.98 g, 6.06 mmol) were dissolved in dichloromethane (8 mL), the catalyst was triflic acid (0.046 g, 0.30 mmol), and MTC-OEt monomer (0.34 g, 1.82 mmol) was dissolved in dichloromethane (12 mL). The MTC-OEt polymerization was stopped at 66.5% conversion. $^1$H NMR (400 MHz, CDCl$_3$): delta 4.48 (s, CH$_2$ poly(MTC-OC$_6$F$_5$), 4H), 4.26 (m, CH$_2$ poly(MTC-OEthyl), 4H), 4.20 (m, CH$_2$CH$_3$ poly(MTC-OEthyl), 2H), 1.51 (s, CH$_3$, 3H) poly(MTC-OC$_6$F$_5$), 1.26 (m, CH$_3$ poly(MTC-OEthyl), 3H), 1.26 (m, CH$_2$CH$_3$ poly (MTC-OEthyl), 3H).

Example 4

Preparation of Pentafluorophenyl Ester Homopolymer P-5 Using Monol Initiator Benzyl Alcohol

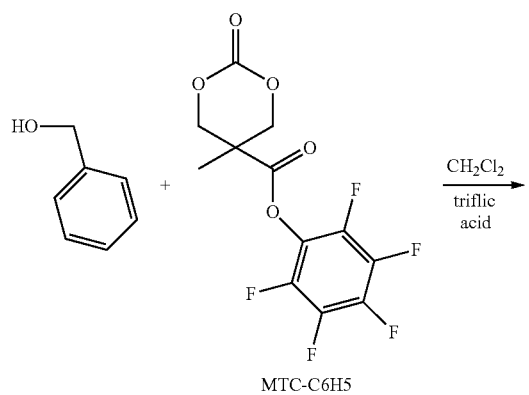

MTC-C6H5

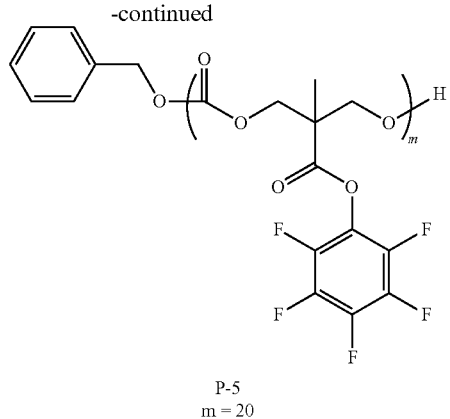

P-5
m = 20

In a nitrogen charged glove box, benzyl alcohol (0.05 g, 0.46 mmol) and MTC-C6F5 monomer (3.02 g, 9.25 mmol) were dissolved in dichloromethane (12 mL). The catalyst, triflic acid (0.069 g, 0.46 mmol), was added and the reaction mixture was stirred at room temperature overnight. The crude polymer solution was precipitated into hexanes, yielding a white solid P-5. From GPC using THF as eluent, Mn=6200, PDI=1.15, DP=20 (m=20 in the above reaction). $^1$H NMR (400 MHz, CDCl$_3$): delta 4.48 (s, 4H, CH$_2$), 1.51 (3H, CH$_3$).

Amide Functionalization

Example 5

Preparation of Amide Polymer A-1

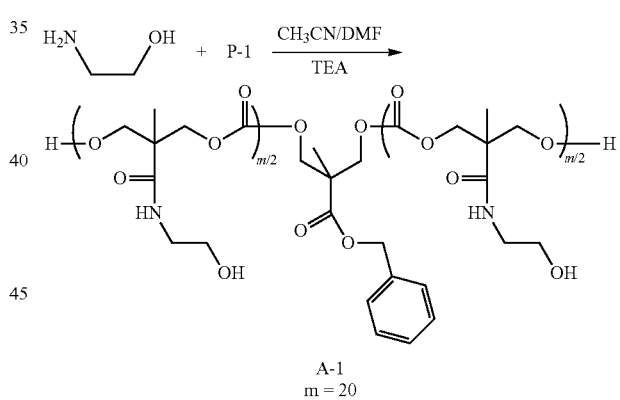

A-1
m = 20

P-1 (200 mg, 0.6132 mmol repeat units) was dissolved in acetonitrile (1 mL). 2-aminoethanol (0.0393 g, 0.6438 mmol) and triethylamine (0.0651 g, 0.6438 mmol) were dissolved in acetonitrile (1 mL) and added dropwise to the polymer solution. A white precipitant began to form. DMF (1 mL) was added to create a clear solution. The reaction was stirred an additional two hours and the crude A-1 was precipitated into diethyl ether. A white solid was recovered and analyzed by GPC using DMF as eluent (see Table 8 below). $^1$H NMR (400 MHz, D$_2$O): delta 4.23 (s, 4H, CH$_2$), 3.53 (2H, CH$_2$OH), 3.26 (t, 2H, NHCH$_2$), 1.19 (s, 3H, CH$_3$).

Examples 6-10

Preparation of Amide Polymers A-2 to A-6

Figure 2:
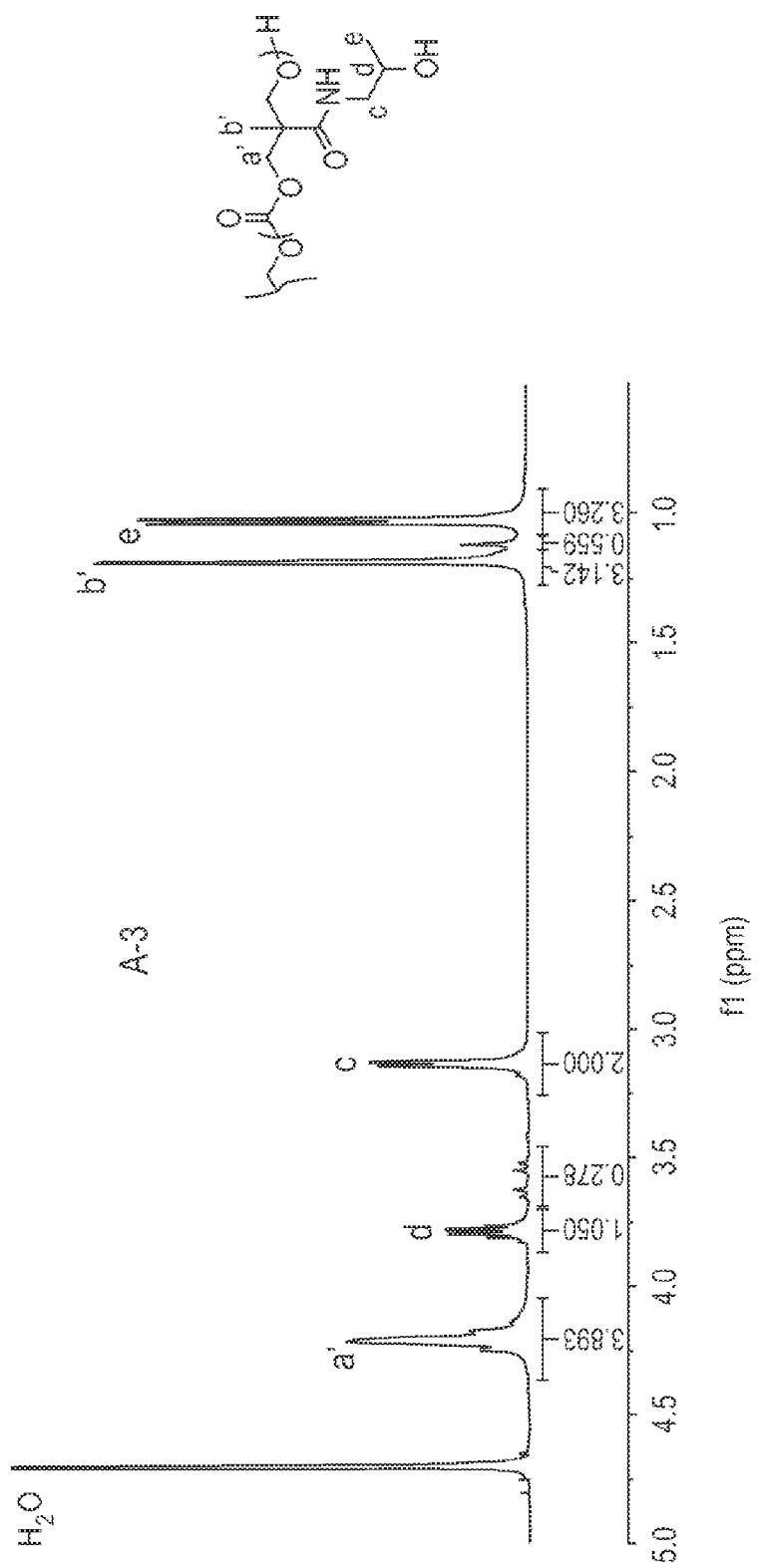
FIG. 2 is a $^1$H NMR spectrum of A-3 formed in Example 7.

These polymers were prepared from P-1 using the general procedure of Example 5 and the amino-alcohols listed in Table 8 below. FIG. 2 is a $^1$H NMR spectrum of A-3 (Example 7). The following are 400 MHz $^1$H NMR peak assignments of Examples 6 to 9 obtained in D$_2$O:

Example 6 delta 4.20 (s, 4H, CH$_2$), 3.51 (t, 2H, CH$_2$OH), 3.20 (t, 2H, NHCH$_2$), 1.62 (t, 2H, CH$_2$CH$_2$CH$_2$), 1.18 (s, 3H, CH$_3$);

Example 7 delta 4.22 (s, 4H, CH$_2$), 3.8 (q, 1H, CHOH), 3.15 (d, 2H, NHCH$_2$), 1.19 (s, 3H, CH$_3$), 1.03 (t, 2H, CHCH$_3$);

Example 8 delta 4.57 (m, 1H, NHCH), 4.19 (s, 4H, CH$_2$), 3.64, 3.23 (m, 2H, CH$_2$OH), 1.58, 1.28 (m, 2H, CH$_2$CH$_3$), 1.19 (s, 3H, CH$_3$), 1.03 (t, 2H, CHCH$_3$); and Example 9 delta 4.23 (s, 4H, CH$_2$), 3.94 (d, 1H, NHCH), 3.56 (t, 2H, CH$_2$OH), 1.21 (s, 3H, CH$_3$).

Table 8 summarizes the structures and properties of the pentafluorophenyl ester polymers P-1 and amide polymers A-1 to A-6. The R' groups of Table 8 refer to the R' the structure below of formula (13):

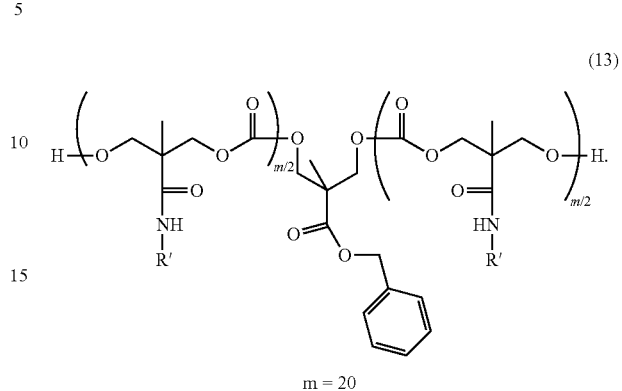

m = 20

The starred bonds of the R' groups of Table 8 are linked to an amide nitrogen. The degree of polymerization m is also listed in Table 8.

TABLE 8

| Example | Name | Amino alcohol used | R' | m | Water Soluble? | GPC Mn | GPC Mw | GPC PDI |
|---|---|---|---|---|---|---|---|---|
| 1 | P-1 | | | 20 | No | 5206 | 5494 | 1.055 |
| 5 | A-1 | 2-Amino-ethanol | *⌒OH | 20 | Yes | 6837 | 7424 | 1.086 |
| 6 | A-2 | 3-Amino-1-propanol | *⌒⌒OH | 20 | Yes | 6207 | 6651 | 1.071 |
| 7 | A-3 | 1-Amino-2-propanol (racemic) | *⌒(OH)CH$_3$ | 20 | Yes | 5625 | 6016 | 1.069 |
| 8 | A-4 | 2-Amino-1-butanol | *CH(Et)CH$_2$OH | 20 | Limited | 6434 | 6977 | 1.08 |
| 9 | A-5 | Serinol | *CH(CH$_2$OH)$_2$ | 20 | Yes | 7084 | 7572 | 1.068 |
| 10 | A-6 | (±)-3-Amino-1,2-propane diol | *CH$_2$CH(OH)CH$_2$OH | 20 | Yes | 5391 | 5713 | 1.06 |

Figure 3:
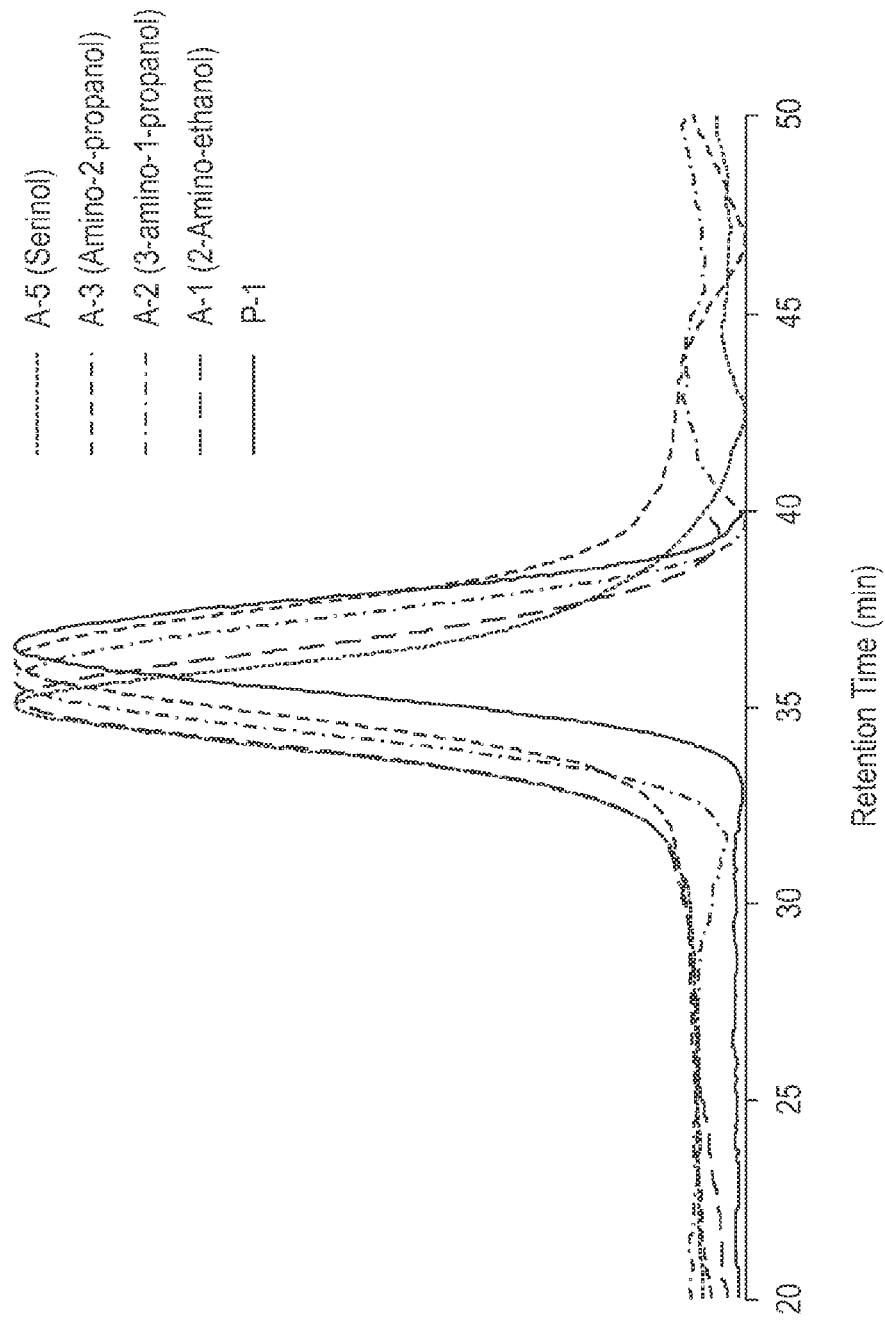
FIG. 3 is a series of gel permeation chromatography (GPC) traces in dimethylformamide (DMF) with 0.5% LiBr of P-1, A-1 to A-3, and A-5 of Table 8.
Figure 4:
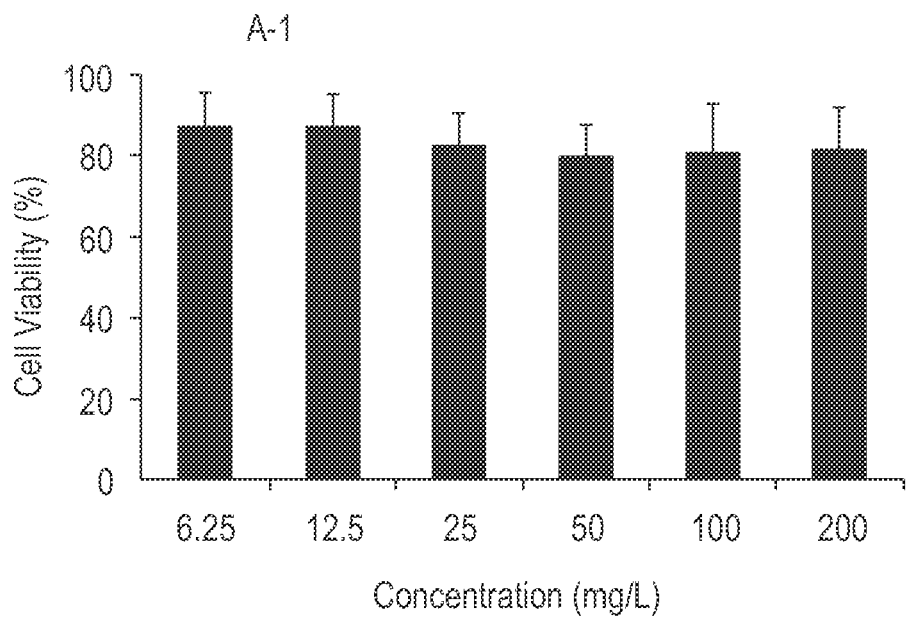
FIG. 4 is a bar chart showing the cell viability of HEK293 cells after 48 hours incubation with A-1.
Figure 5:
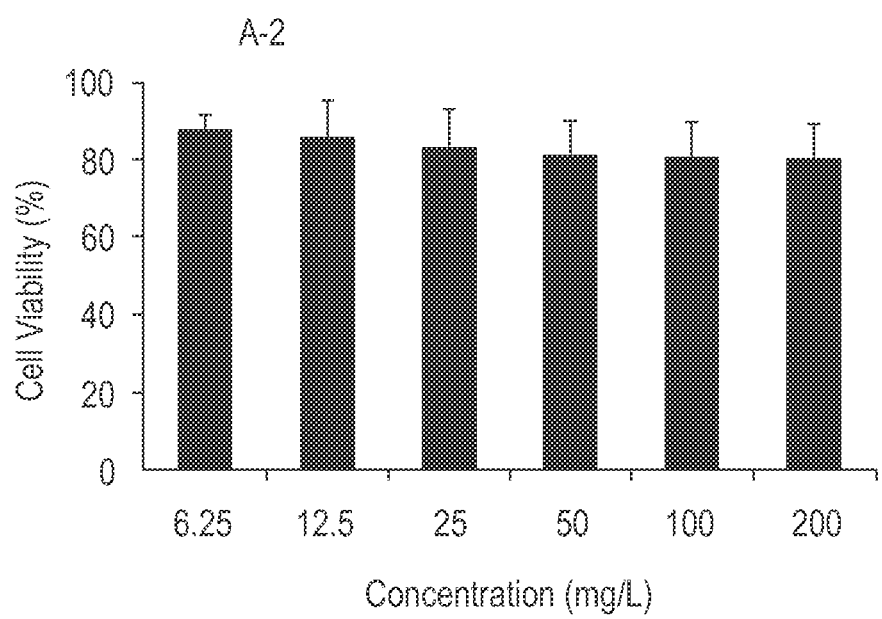
FIG. 5 is a bar chart showing the cell viability of HEK293 cells after 48 hours incubation with A-2.
Figure 6:
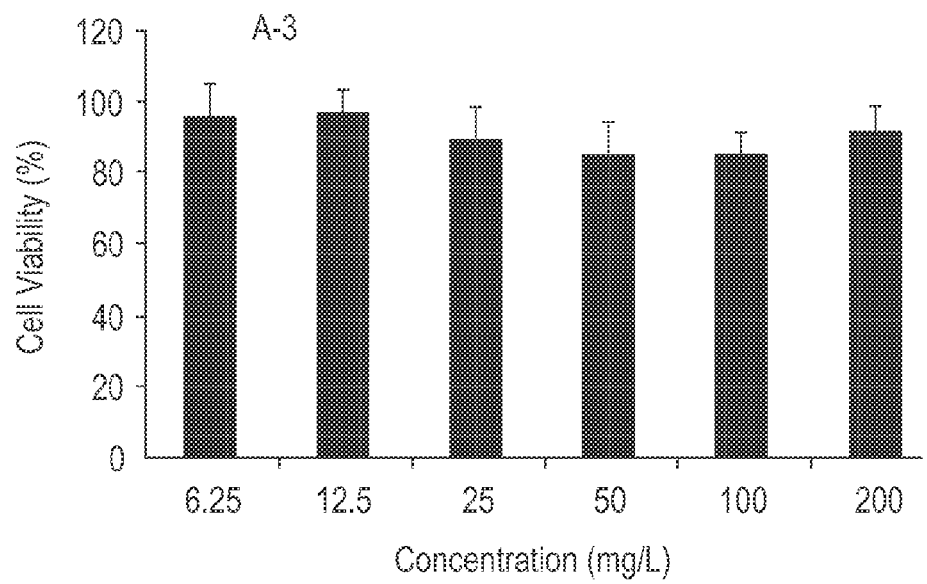
FIG. 6 is a bar chart showing the cell viability of HEK293 cells after 48 hours incubation with A-3.
Figure 7:
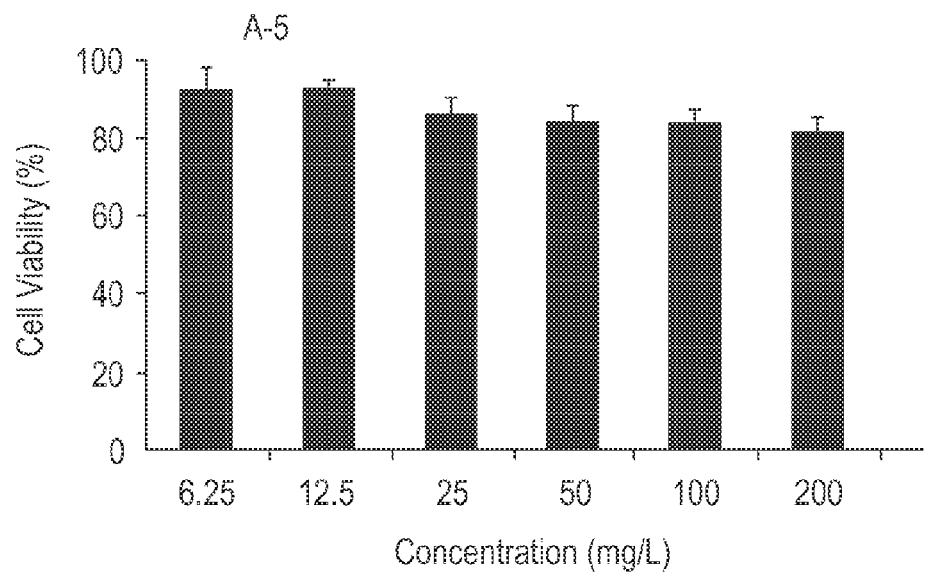
FIG. 7 is a bar chart showing the cell viability of HEK293 cells after 48 hours incubation with A-5.
Figure 8:
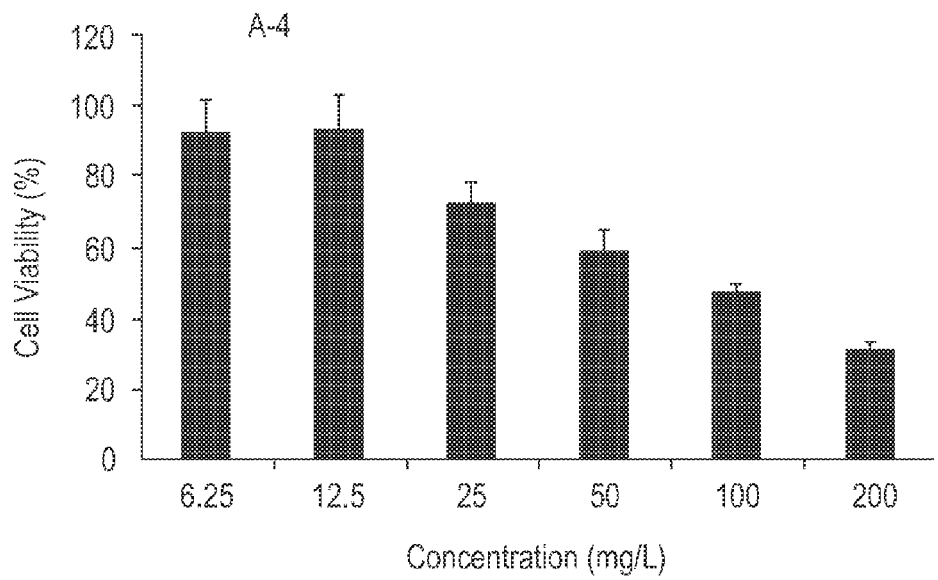
FIG. 8 is a bar chart showing the cell viability of HEK293 cells after 48 hours incubation with A-4.
Figure 9:
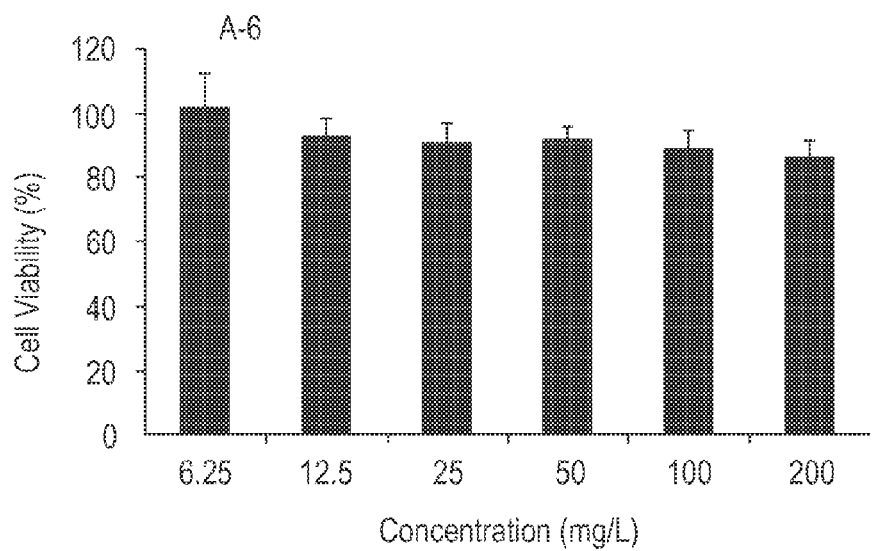
FIG. 9 is a bar chart showing the cell viability of HEK293 cells after 48 hours incubation with A-6.

Polymer P-1 and the amide-containing polymers A-1 to A-3 and A-5 of Table 8 were also analyzed by gel permeation chromatography (GPC) to determine if there was any degradation of the backbone during amide formation. As shown by the DMF GPC traces in FIG. 3, there was no broadening of the peak and no significant drop in polymer molecular weight.

To determine polymer water solubility, purified polymer was placed in a small vial and water was added to dissolve the amide-containing polymer. A-4 (Example 7), prepared with 2-aminobutanol, had limited water solubility but all other amide-containing polymers (A-1, A-2, A-3, A-5, and A-6) were fully water soluble.

Examples 11-20

Preparation of Diblock Polymers D-1 to D-10

These polymers were prepared from P-3 (Example 2) or P-4 (Example 3) using the general procedure of Example 4 and the amino-alcohols listed in Table 9 below.

Table 9 summarizes the properties of diblock copolymers D-1 to D-10 and the precursor polymers P-3 and P-4. Subscripts m and n of Table 9 and the R' groups of Table 9 refer to m, n, and R', respectively, of the structure of formula (14):

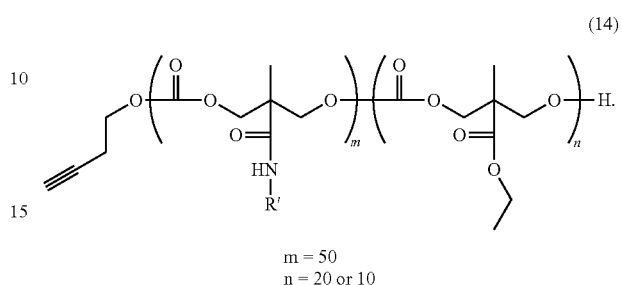

$m = 50$
$n = 20$ or $10$

The starred bonds of the R' groups of Table 9 are linked to an amide nitrogen.

TABLE 9

| Example | Name | Amino alcohol used | R' | A Block (m) | B Block (n) | Water Soluble? | NMR Mn | NMR Mw | GPC PDI |
|---|---|---|---|---|---|---|---|---|---|
| 2 | P-3[a] | | | 50 | 20 | No | A Block: 10100<br>B Block: 12800 | A Block: 11600<br>B Block: 15200 | A Block: 1.15<br>B Block: 1.18 |
| 3 | P-4[a] | | | 50 | 10 | No | A Block: 10500<br>B Block: 12600 | A Block: 11900<br>B Block: 14700 | A Block: 1.14<br>B Block: 1.16 |
| 11 | D-1 | 2-Aminoethanol | *\_\_/OH | 50 | 20 | Yes | ND | ND | ND |
| 12 | D-2 | 2-Aminoethanol | *\_\_/OH | 50 | 10 | Yes | ND | ND | ND |
| 13 | D-3 | 3-Amino-1-propanol | *\_\_\_/OH | 50 | 20 | Yes | ND | ND | ND |
| 14 | D-4 | 3-Amino-1-propanol | *\_\_\_/OH | 50 | 10 | Yes | ND | ND | ND |
| 15 | D-5 | 1-Amino-2-propanol (racemic) | *\_/OH | 50 | 20 | Yes | ND | ND | ND |
| 16 | D-6 | 1-Amino-2-propanol (racemic) | *\_/OH | 50 | 10 | Yes | ND | ND | ND |

TABLE 9-continued

| Example | Name | Amino alcohol used | R' | A Block (m) | B Block (n) | Water Soluble? | NMR Mn | NMR Mw | GPC PDI |
|---|---|---|---|---|---|---|---|---|---|
| 17 | D-7 | Serinol | 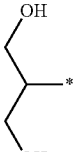 | 50 | 20 | Yes | ND | ND | ND |
| 18 | D-8 | Serinol | 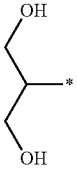 | 50 | 10 | Yes | ND | ND | ND |
| 19 | D-9 | (±)-3-Amino-1,2-propane diol | 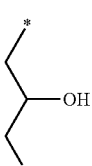 | 50 | 20 | Yes | ND | ND | ND |
| 20 | D-10 | (±)-3-Amino-1,2-propane diol | 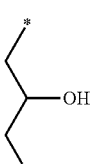 | 50 | 10 | Yes | ND | ND | ND |

[a] GPC run in THF, all others run in DMF
ND = not determined

Examples 21-25

Preparation of Amide Homopolymers A-7 to A-11

These polymers were prepared from P-5 using the general procedure of Example 5 and the amino-alcohols listed in Table 10 below. The following are 400 MHz $^1$H NMR peak assignments of Examples 21 to 25 obtained in $D_2O$:

Example 21 delta 4.23 (s, 4H, $CH_2$), 3.53 (2H, $CH_2OH$), 3.26 (t, 2H, $NHCH_2$), 1.19 (s, 3H, $CH_3$);

Example 22 delta 4.20 (s, 4H, $CH_2$), 3.51 (t, 2H, $CH_2OH$), 3.20 (t, 2H, $NHCH_2$), 1.62 (t, 2H, $CH_2CH_2CH_2$), 1.18 (s, 3H, $CH_3$);

Example 23 delta 4.22 (s, 4H, $CH_2$), 3.8 (q, 1H, CHOH), 3.15 (d, 2H, $NHCH_2$), 1.19 (s, 3H, $CH_3$), 1.03 (t, 2H, $CHCH_3$);

Example 24 delta 4.23 (s, 4H, $CH_2$), 3.94 (d, 1H, NHCH), 3.56 (t, 2H, $CH_2OH$), 1.21 (s, 3H, $CH_3$); and

Example 25 delta 4.19 (m, 4H, $CH_2$), 3.66 (m, 1H, CHOH), 3.37 (dm, 2H, $NHCH_2$), 1.19 (s, 3H, $CH_3$), 1.03 (t, 2H, $CHCH_3$).

Table 10 summarizes the structures and properties of the pentafluorophenyl ester polymer P-5 and amide polymers A-7 to A-11. The R' groups of Table 10 refer to the R' groups of formula (15):

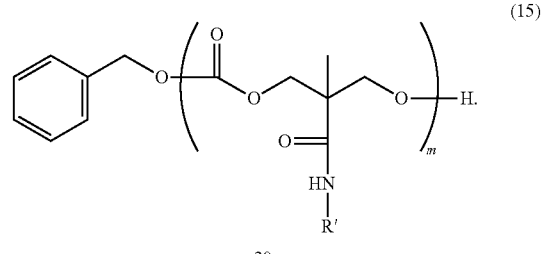

$m = 20$ (15)

The starred bond of the R' group in Table 10 is linked to an amide nitrogen. The degree of polymerization m is also listed in Table 10.

TABLE 10

| Example | Name | Amino alcohol used | R' | m | Water Soluble? | GPC Mn | GPC Mw | GPC PDI |
|---|---|---|---|---|---|---|---|---|
| 1 | P-5[a] | | | 20 | No | 6200 | 7100 | 1.15 |
| 21 | A-7 | 2-Amino-ethanol | *–CH₂CH₂–OH | 20 | Yes | ND | ND | ND |
| 22 | A-8 | 3-Amino-1-propanol | *–CH₂CH₂CH₂–OH | 20 | Yes | ND | ND | ND |
| 23 | A-9 | 1-Amino-2-propanol (racemic) | *–CH₂–CH(CH₃)–OH | 20 | Yes | ND | ND | ND |
| 24 | A-10 | Serinol | –CH(CH₂OH)₂ with * on central C | 20 | Yes | ND | ND | ND |
| 25 | A-11 | (±)-3-Amino-1,2-propane diol | *–CH₂–CH(OH)–CH₂OH | 20 | Yes | ND | ND | ND |

[a] GPC run in THF, all others run in DMF
ND = not determined

Cell Viability

Cell viability studies were performed using the amide-containing polymers of Table 8 and HEK293 cells. Two PEG homopolymer of 5,000 Da and 10,000 Da were used as controls.

HEK293 cells were cultured in RPMI-1640 supplied with 10% fetal bovine serum (FBS) and 1% penicillin-streptomycin. HEK293 cells were seeded onto 96-well plates at a density of 10,000 cells/well. The cells were incubated at 37° C., 5% $CO_2$. After 24 hours, the medium was replaced with fresh medium containing polymer at various concentrations. After 48 hours incubation, 100 microliters of fresh medium and 20 microliters of 5 mg/mL MTT solution were used to replace the sample medium. After 4 hours incubation, the medium was removed, and DMSO (150 microliters) was added to each well to dissolve the formazan crystals. The absorbance of each well was measured as that at 550 nm deducted by that at 690 nm with a microplate reader (Power-Wave X, Bio-tek Instruments, U.S.A.). The results were presented as a percentage of absorbance of the blank control.

Figure 10:
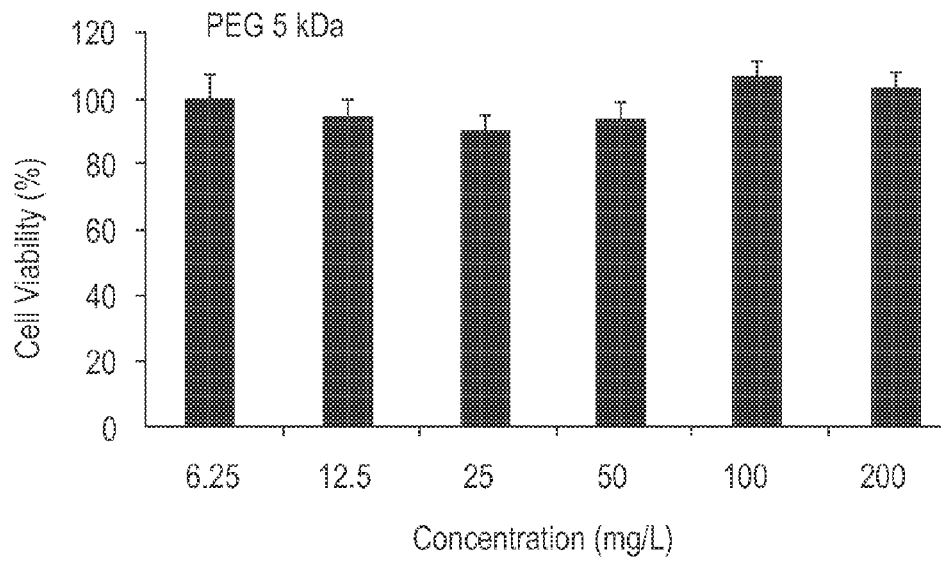
FIG. 10 is a bar chart showing the cell viability of HEK293 cells after 48 hours incubation with PEG 5 kDa.
Figure 11:
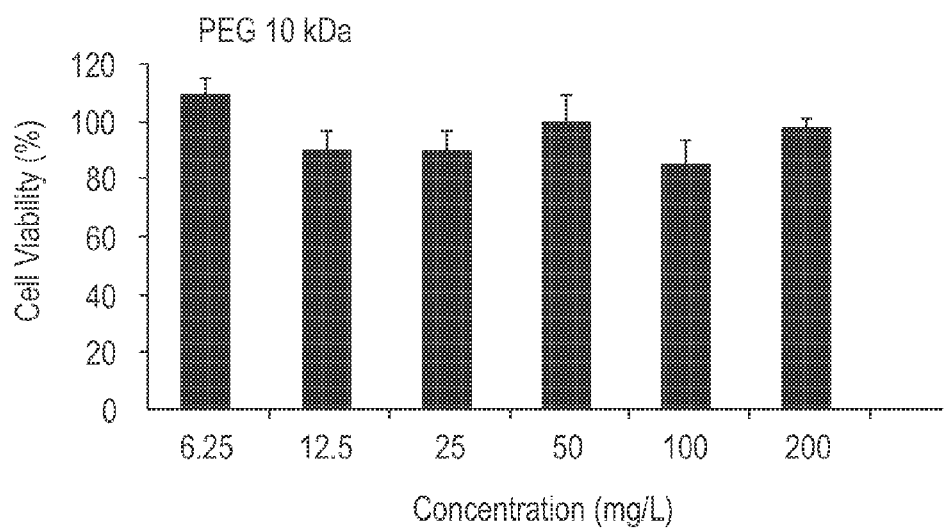
FIG. 11 is a bar chart showing the cell viability of HEK293 cells after 48 hours incubation with PEG 10 kDa.

As shown in FIGS. 4-9 (for A-1, A-3, A-2, A-4, A-5, and A-6, respectively), only the polymer substituted with 2-amino-1-butanol (A-4) had cell viability dropping below 80%. All other polymers were non-toxic, showing toxicity profiles comparable to the PEG 5 kDa (FIG. 10) and PEG 10 kDa (FIG. 11).

Mouse Intravenous LD50 Studies

Female Balb/c mice (19-21 g) were randomly selected and kept in cages for at least 5 days to allow for acclimatization to the laboratory conditions. Mice were fasted for 12 hours before testing. The dose of the polymer was 500 mg/kg. Polymer was dissolved in sterilized saline at a concentration of 50 mg/mL for injection and administered via the intravenous injection. Polymer solution was firstly given to one mouse. If the first mouse survived after 48 hours, two more mice were further used for the test. After injection, all the animals were observed every 30 minutes for the first 4 hours and daily thereafter, for a total of 14 days.

Preliminary animal data for the amide-containing polymer A-5 (Example 8) of Table 8 substituted with serinol indicate that the polymer was non-toxic at concentrations>500 mg/kg.

Polymer Stealth

One method of determining if a polymer system has stealth characteristics is to look at the stability of a serum solution containing the polymer. Using dynamic light scattering, the sizes of particles formed in the serum can be measured with time. If the initial particle size remains consistent over time (i.e., the serum solution does not show unacceptable flocculation with time), it can be assumed that the polymer has stealth characteristics. The synthetic polymer and/or the serum components can flocculate.

The amide-containing polymers of Table 8 and Table 9 were dissolved in phosphate buffered saline (PBS) containing 10% FBS. The concentration of each polymer was 500 mg/L. The time dependent particle sizes of the serum solutions were analyzed by dynamic light scattering using a Zetasizer 3000 HAS (Malvern Instrument Ltd., Malvern, UK) equipped with a He—Ne laser beam at 658 nm (scattering angle: 90°) for a 24 hour period or 48 hour period. Each sample was measured 3 times and an average particle size was obtained. The particle size is reported as the average circular diameter in nanometers.

Figure 12:
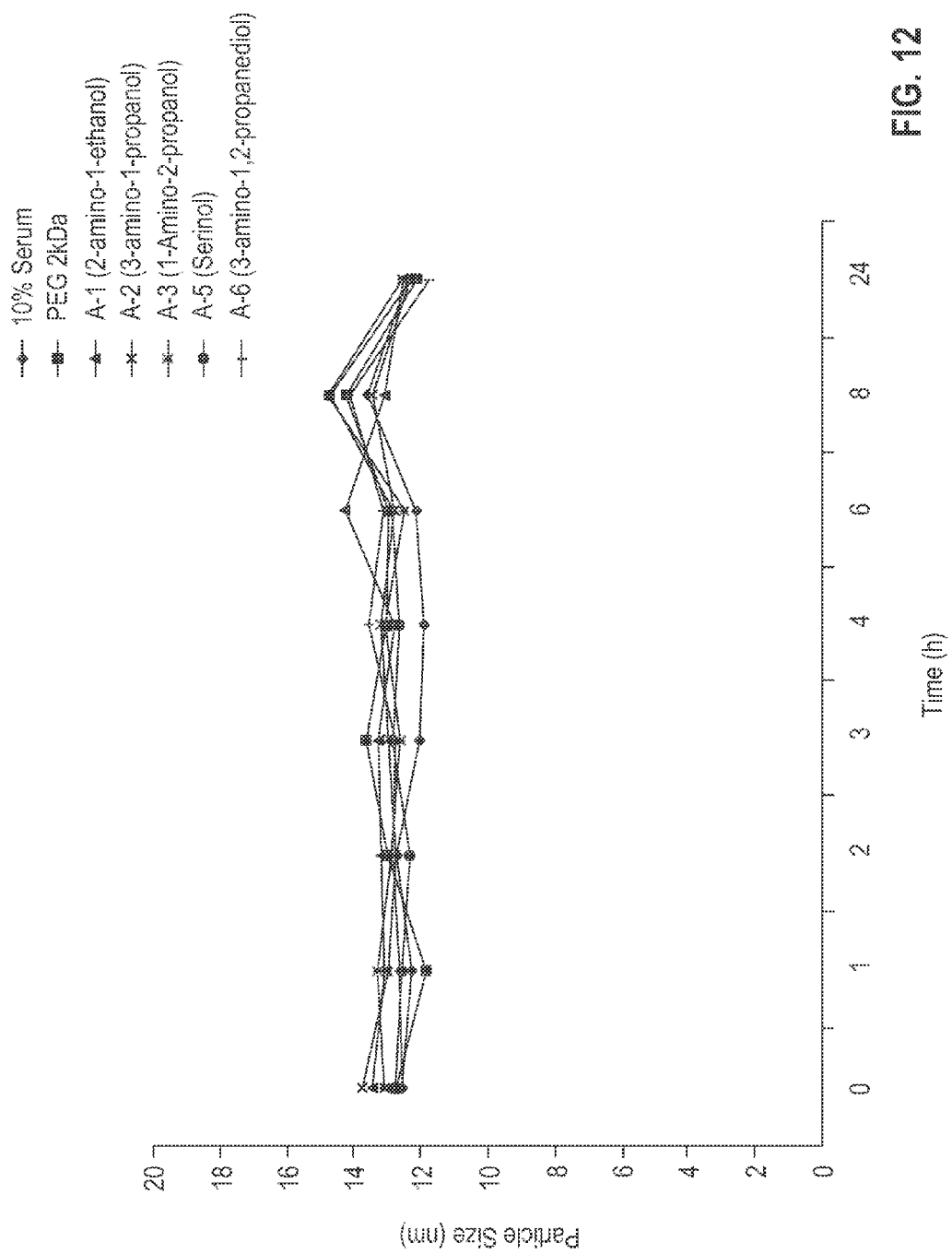
FIG. 12 is a graph showing the particle size behavior as a function of time of 10% fetal bovine serum (FBS) containing polymers A-7, A-8, A-9, A-10, and A-11, respectively of Table 10. PEG 2 kDa and 10% serum were used as controls.

FIG. 12 is a graph showing the particle size behavior of several polymers of Table 10 in PBS/10% FBS as a function of time. PEG 2 kDa and 10% serum were used as controls. The particle size remains constant over a 24 hour period for each sample, indicating that no flocculation was caused by polymers A-7, A-8, A-9, A-10, and A-11. The average particle size observed for each sample was in a range of 10 nm to 15 nm.

Figure 13:
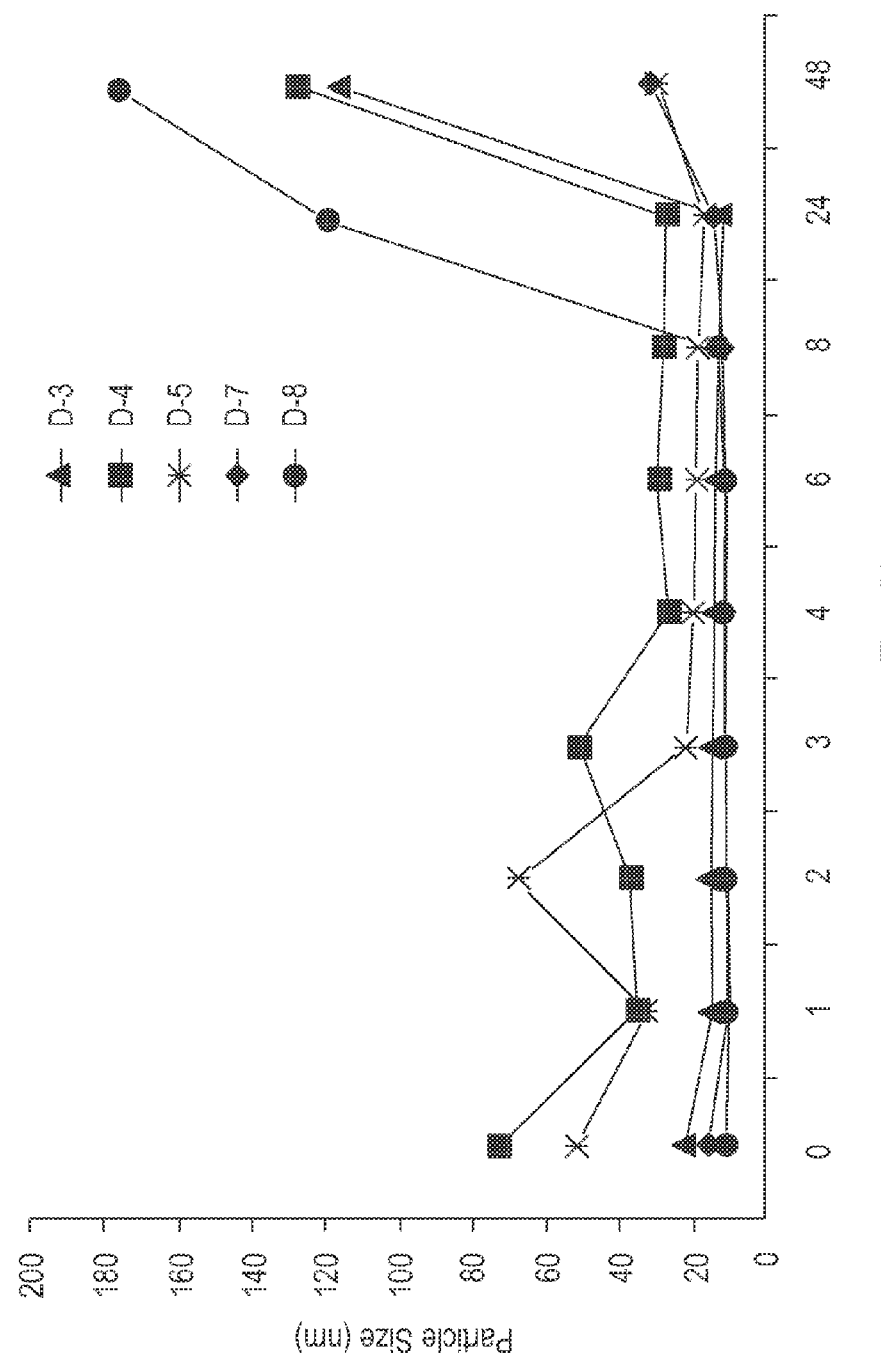
FIG. 13 is a graph showing the particle size behavior (measured by dynamic light scattering) as a function of time of 10% FBS containing diblock polymers D-3 (derived from 3-amino propanol, m=50, n=20), D-4 (derived from 3-amino propanol, m=50, n=10), D-5 (derived from 1-amino-2-propanol, m=50, n=20), D-7 (derived from serinol, m=50, n=20), and D-8 (derived from serinol, m=50, n=10), respectively, of Table 9.

FIG. 13 is a graph showing the particle size behavior as a function of time in PBS/10% FBS of the following diblock polymers of Table 9: D-3 (derived from 3-amino propanol, m=50, n=20), D-4 (derived from 3-amino propanol, m=50, n=10), D-5 (derived from 1-amino-2-propanol, m=50, n=20), D-7 (derived from serinol, m=50, n=20), and D-8 (derived from serinol, m=50, n=10). No significant flocculation below 8 hours was observed for these polymers. The average particle size obtained using D-3 and D-7 was in a range of about 10 nm to 20 nm for the first 24 hours, and rose thereafter to about 110 nm and about 30 nm, respectively, at 48 hours. The average particle size obtained using D-8 was in a range of about 10 nm to 20 nm for 8 hours and rose thereafter to about 170 nm at 48 hours. The average particle size obtained using D-4 fluctuated between 75 nm and about 30 nm in the first 24 hours, and rose thereafter to about 130 nm at 48 hours. The average particle size obtained using D-5 fluctuated between 70 nm and about 20 nm in the first 3 hours, and thereafter remained less than 30 nm up to 48 hours.

Figure 14:
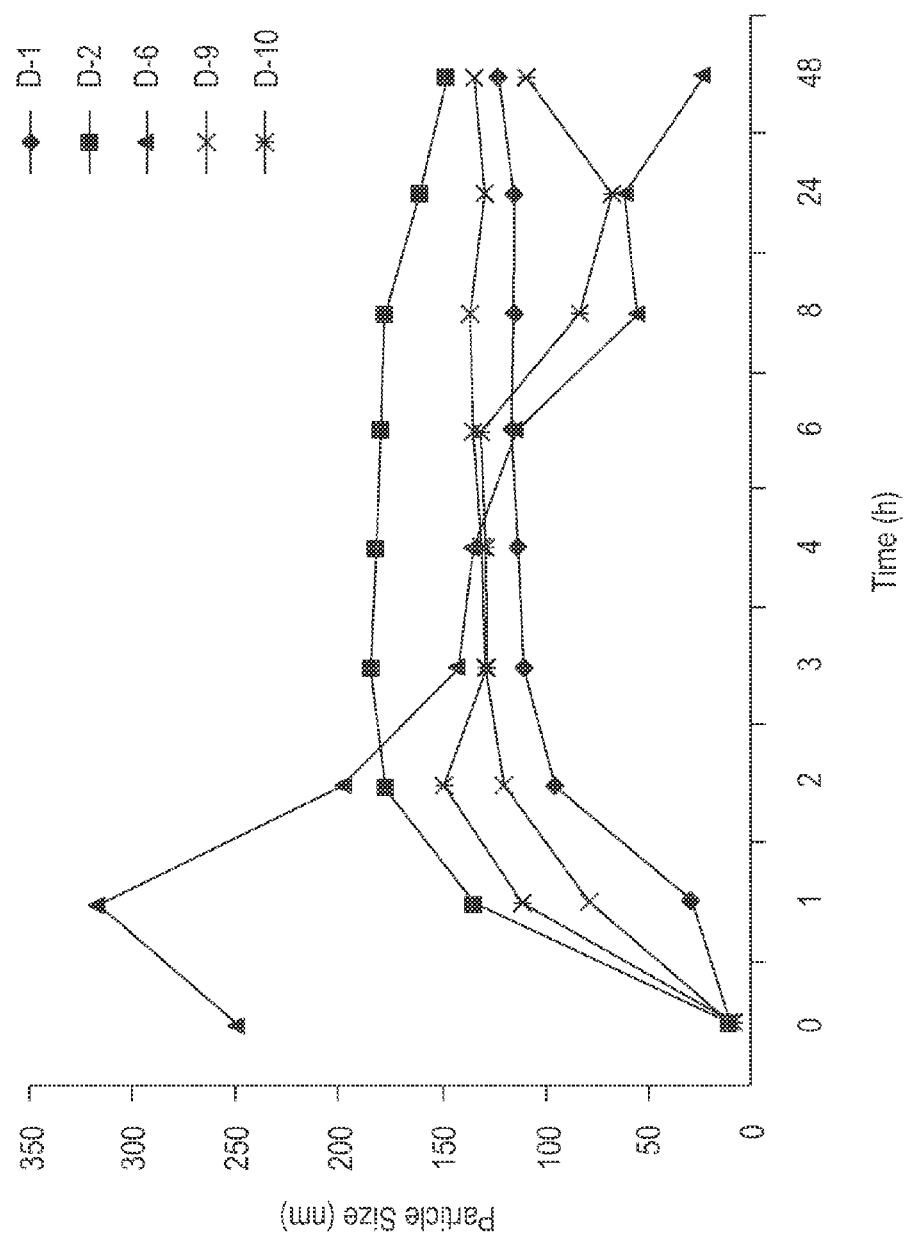
FIG. 14 is a graph showing the particle size behavior (measured by dynamic light scattering) as a function of time of 10% FBS containing diblock polymers D-1 (derived from 2-amino ethanol, m=50, n=20), D-2 (derived from 2-amino ethanol, m=50, n=10), D-6 (derived from 1-amino-2-propanol, m=50, n=20), D-9 (derived from (±)-3-amino-1,2-propane diol, m=50, n=20), and D-10 (derived from (±)-3-amino-1,2-propane diol, m=50, n=10), respectively, of Table 9.

FIG. 14 is a graph showing the particle size behavior as a function of time in PBS/10% FBS of the following diblock polymers of Table 9: D-1 (derived from 2-amino ethanol, m=50, n=20), D-2 (derived from 2-amino ethanol, m=50, n=10), D-6 (derived from 1-amino-2-propanol, m=50, n=20), D-9 (derived from (±)-3-Amino-1,2-propane diol, m=50, n=20), and D-10 (derived from (±)-3-amino-1,2-propane diol, m=50, n=10). The average particle size obtained using D-1 rose to a plateau of about 100 nm in the first 3 hours, which extended to 48 hours. The average particle size obtained using D-2 rose to a peak of about 175 nm, which decreased to about 150 nm at 48 hours. The average particle size obtained using D-6 rose to a peak of about 325 nm at 1 hour, which decreased thereafter to about 20 nm at 48 hours. The average particle size obtained using D-9 rose to a plateau of about 120 nm in the first 3 hours, which extended to 48 hours. The average particle size obtained using D-10 rose to a peak of about 150 nm in the first 2 hours, which fell to about 130 nm at 48 hours.

The particle size data for the Table 8 series of polymers indicate that polycarbonates comprising a majority of non-charged hydrophilic repeat units bearing one or or two hydroxy groups are non-toxic and possess stealth properties in serum, making these polymers attractive as dispersants for hydrophobic therapeutic agents. A monol, diol, or a mixture thereof can be employed as the initiator for the ring opening polymerization. Each of the hydrophilic carbonate repeat units has an amide side chain wherein the amide carbonyl is linked to the polymer backbone. The amide side chain can comprise 3 to 5 carbons, 1 amide group, and 1 to 2 hydroxy groups. Preferably, the amide side chain comprises 2 hydroxymethylene groups (*—CH$_2$—OH).

The particle size data for the Table 9 series of polymers, which comprise a non-charged hydrophobic second polymer block, indicate these polymers can also possess stealth properties with respect to serum components. Less flocculation was observed for D-7 and D-8 compared to D-9 and D-10, indicating that a side chain containing two hydroxymethylene groups may be more compatible with serum components compared to a diol side chain that contains one hydroxymethylene group and one hydroxymethine group:

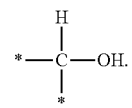

Therefore, the Table 9 polymers are also attractive as dispersants for hydrophobic therapeutic agents (e.g., genes, proteins, peptides, drugs, and combinations thereof). The hydrophilic repeat units can be used in combination. The hydrophobic repeat units can also be used in combination.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A polymer comprising a polymer chain, the polymer chain comprising a carbonate repeat unit of formula (1):

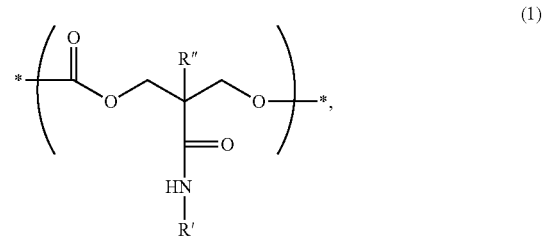

wherein
the polymer chain has a polycarbonate or a polyestercarbonate backbone,

R' is a monovalent radical comprising 2 to 4 carbons and 1 to 2 hydroxy groups,

R" is a monovalent radical selected from the group consisting of hydrogen, methyl, ethyl, and propyl, the polymer is non-charged, and the polymer is soluble in water.

2. The polymer of claim 1, wherein R' is selected from the group consisting of

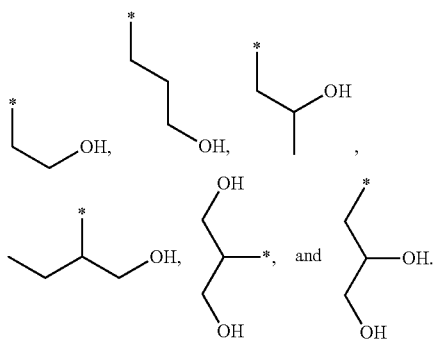

3. The polymer of claim 1, wherein the polymer has a number average molecular weight (Mn) of about 1500 or more.

4. The polymer of claim 1, wherein the polymer has a mouse intravenous LD50 value of greater than 500 mg/kg.

5. The polymer of claim 1, wherein the polymer is biodegradable in accordance with ASTM D6400.

6. The polymer of claim 1, wherein the polymer chain is a homopolymer of the carbonate repeat unit.

7. The polymer of claim 6, wherein the polymer has a structure according to formula (1a):

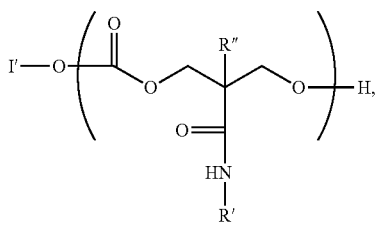

wherein m is a number having an average value greater than 1,

I' is a monovalent radical comprising 1 to 20 carbons, each R" is an independent monovalent radical selected from the group consisting of hydrogen, methyl, ethyl, and propyl, and each R' is an independent monovalent radical selected from the group consisting of:

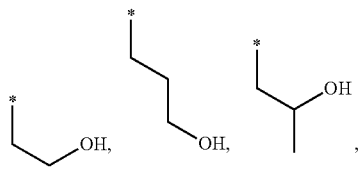

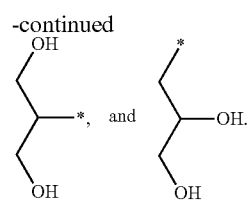

8. The polymer of claim 1, wherein the polymer chain is a random copolymer of the carbonate repeat unit and a non-charged hydrophobic second repeat unit.

9. The polymer of claim 8, wherein the polymer is a random copolymer having a structure according to formula (2):

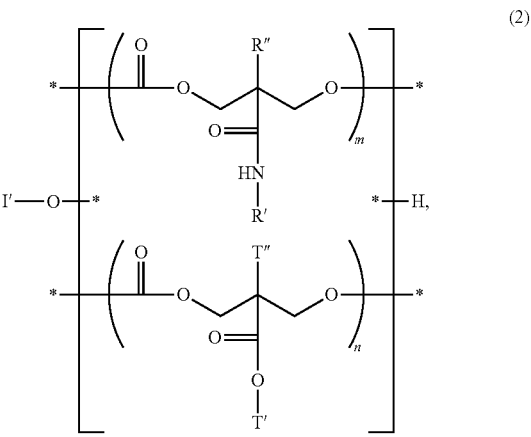

wherein m is a number having an average value greater than 1, n is a number having an average value greater than 1, each T' is an independent monovalent radical comprising 1 to 6 carbons, each T" is an independent monovalent radical selected from the group consisting of alkyl groups comprising 1 to 30 carbons and aryl groups comprising 6 to 30 carbons, each R" is an independent monovalent radical selected from the group consisting of hydrogen, methyl, ethyl, and propyl, I' is a monovalent group comprising 1 to 20 carbons, and each R' is selected from the group consisting of:

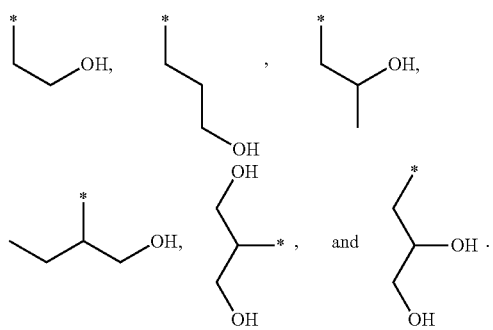

10. The polymer of claim 1, wherein the polymer is a diblock copolymer comprising a first block linked to a second block, the first block comprises the polymer chain comprising the carbonate repeat unit, and the second block comprises a non-charged hydrophobic second repeat unit.

11. The polymer of claim 10, wherein the polymer is a diblock copolymer having a structure according to formula (3):

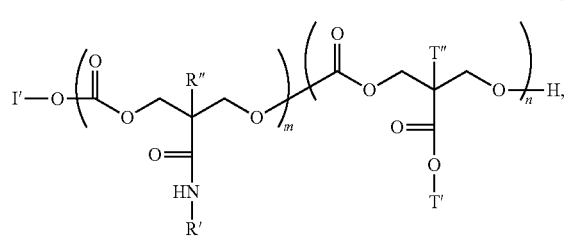

(3)

wherein
m is a number having an average value greater than 1,
n is a number having an average value greater than 1,
I' is a monovalent radical comprising 1 to 20 carbons,
each R" is an independent monovalent radical selected from the group consisting of hydrogen, methyl, ethyl, and propyl,
each T" is an independent monovalent radical selected from the group consisting of hydrogen, methyl, ethyl, and propyl,
each T' is an independent monovalent radical selected from the group consisting of alkyl groups comprising 1 to 30 carbons and aryl groups comprising 6 to 30 carbons, and
each R' is an independent monovalent radical selected from the group consisting of:

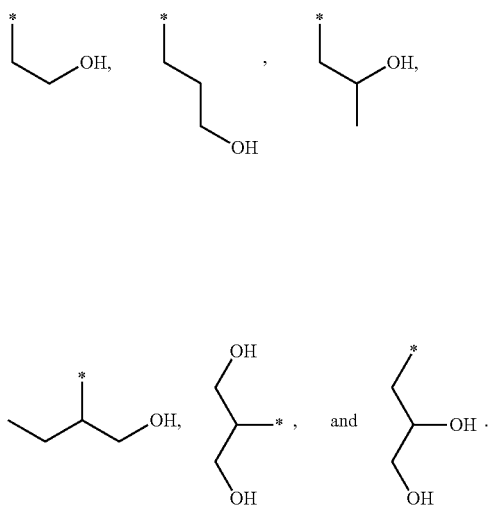

12. The polymer of claim 1, wherein the polymer comprises a second polymer chain, the second polymer chain comprising the carbonate repeat unit and having a polycarbonate backbone or a polyestercarbonate backbone, wherein said polymer chain and the second polymer chain are linked by respective terminal repeat units to a divalent linking group having a structure *—O—I"—O—*, wherein I" comprises 2-20 carbons.

13. The polymer of claim 12, wherein the polymer has a structure according to formula (4):

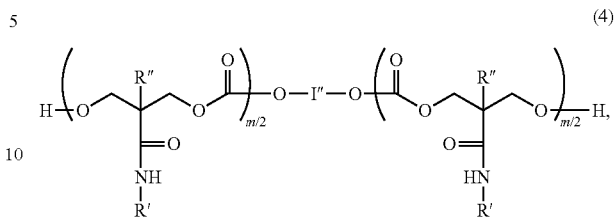

(4)

wherein
m is a number having an average value greater than 1,
I" is a divalent linking group comprising 2 to 20 carbons, and
each R" is an independent monovalent radical selected from the group consisting of hydrogen, methyl, ethyl, and propyl, and
each R' is an independent monovalent radical selected from the group consisting of:

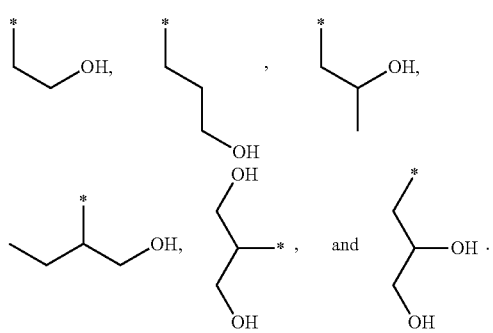

14. The polymer of claim 1, wherein R" is methyl.
15. The polymer of claim 1, wherein the carbonate repeat unit is stereospecific.
16. A composition comprising:
the polymer of claim 1; and
a therapeutic agent for a medical treatment, the therapeutic agent selected from the group consisting of genes, proteins, peptides, drugs, and combinations thereof;
wherein
the polymer and the therapeutic agent are bound by non-covalent interactions,
the composition is dispersible in water as a particle having an average circular diameter of about 10 nm to about 500 nm, and
an aqueous mixture of the composition is suitable for intravenous injection.
17. The composition of claim 16, wherein the polymer has a structure according to formula (4):

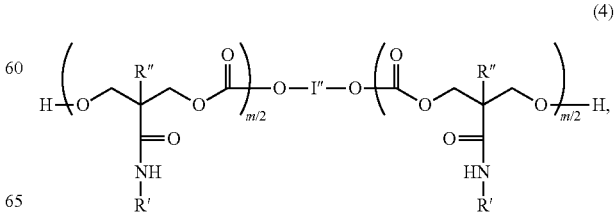

(4)

wherein m is a number having an average value greater than 1,

I" is a divalent linking group comprising 2 to 20 carbons, and each R" is an independent monovalent radical selected from the group consisting of hydrogen, methyl, ethyl, and propyl, and each R' is an independent monovalent radical selected from the group consisting of

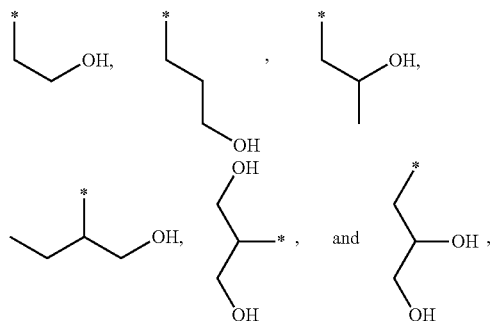

and the polymer is soluble in water.

18. The composition of claim 17, wherein m has an average value of about 20 to about 50.

19. The composition of claim 16, wherein the polymer has a number average molecular weight (Mn) of about 5000 to about 10000.

20. The composition of claim 16, wherein the polymer is a diblock copolymer having a structure according to formula (3):

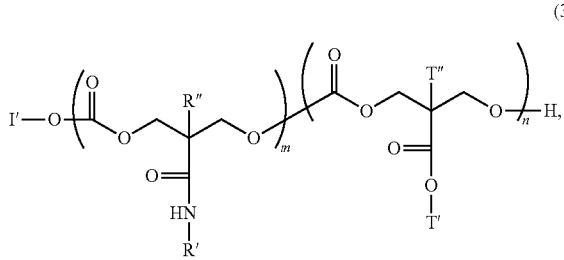

wherein m is a number having an average value greater than 1, n is a number having an average value greater than 1, I' is a monovalent radical comprising 1 to 20 carbons, each R" is an independent monovalent radical selected from the group consisting of hydrogen, methyl, ethyl, and propyl, each T" is an independent monovalent radical selected from the group consisting of hydrogen, methyl, ethyl, and propyl, each T' is an independent monovalent radical selected from the group consisting of alkyl groups comprising 1 to 30 carbons and aryl groups comprising 6 to 30 carbons, and each R' is an independent monovalent radical selected from the group consisting of:

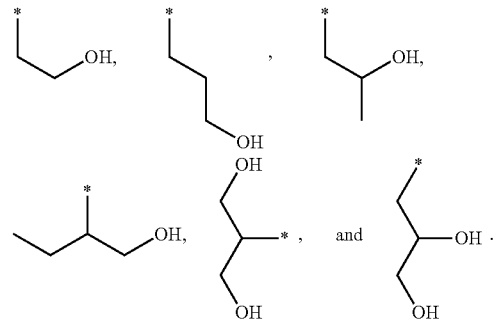

21. A method, comprising:

forming a first mixture comprising water and a non-charged polymer comprising a polymer chain, the polymer chain comprising a carbonate repeat unit of formula (1):

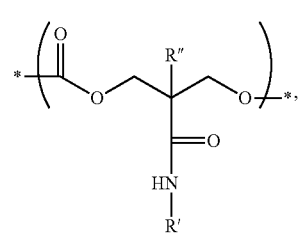

wherein i) R' is monovalent radical comprising 2 to 4 carbons and 1 to 2 hydroxy groups, ii) R" is a selected from the group consisting of hydrogen, methyl, ethyl, and propyl, iii) the polymer chain has a polycarbonate backbone or a polyestercarbonate backbone, and (iv) the polymer is soluble in the water;

forming a second mixture comprising i) a solvent selected from the group consisting of organic solvents, water, and combinations thereof and ii) a therapeutic agent for a medical treatment, the therapeutic agent selected from the group consisting of a genes, proteins, peptides, drugs, and combinations thereof;

combining the first mixture and the second mixture, thereby forming a third mixture; and removing organic solvent from the third mixture, thereby forming a particle comprising the polymer and the therapeutic agent bound by non-covalent interactions, wherein the particle is dispersible in water, and an aqueous mixture of the particle is suitable for intravenous injection.

22. The method of claim 21, wherein R' is

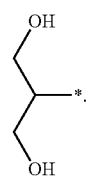

23. The method of claim 21, wherein the polymer has a structure according to formula (4):

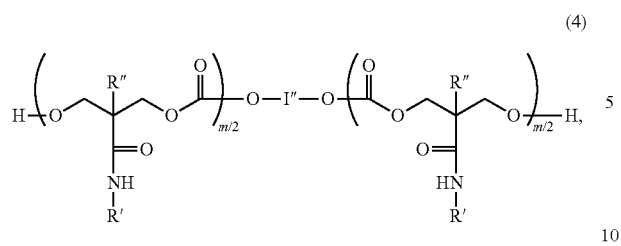
(4)

wherein
   m is a number having an average value greater than 1,
   I″ is a divalent linking group comprising 2 to 20 carbons,
   each R″ is an independent monovalent radical selected from the group consisting of hydrogen, methyl, ethyl, and propyl, and
   each R′ is an independent monovalent radical selected from the group consisting of

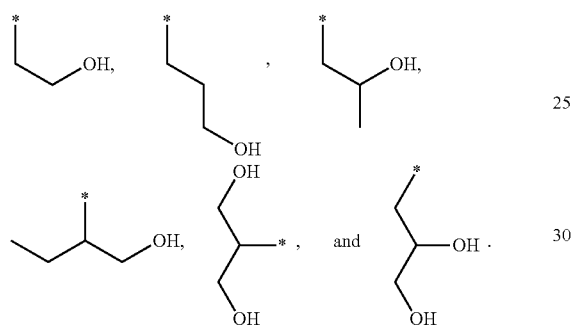

24. The method of claim 21, wherein the polymer is a diblock polymer having a structure according to formula (3):

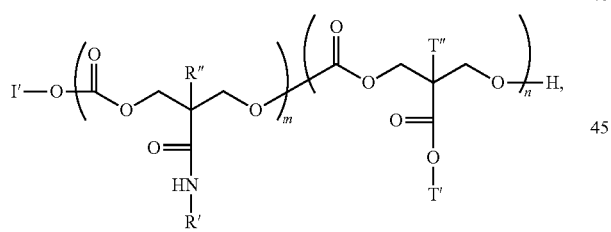
(3)

wherein
   m is a number having an average value greater than 1,
   n is a number having an average value greater than 1,
   I′ is a monovalent radical comprising 1 to 20 carbons,
   each R″ is an independent monovalent radical selected from the group consisting of hydrogen, methyl, ethyl, and propyl,
   each T″ is an independent monovalent radical selected from the group consisting of hydrogen, methyl, ethyl, and propyl,
   each T′ is an independent monovalent radical selected from the group consisting of alkyl groups comprising 1 to 30 carbons and aryl groups comprising 6 to 30 carbons, and
   each R′ is an independent monovalent radical selected from the group consisting of:

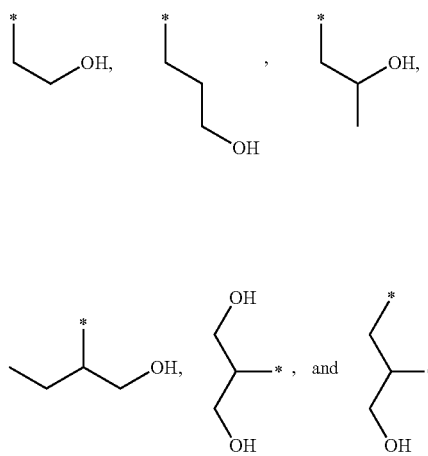

25. The polymer of claim 1, wherein R′ is

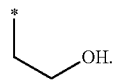

26. The polymer of claim 1, wherein R′ is

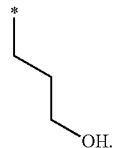

27. The polymer of claim 1, wherein R′ is

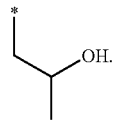

28. The polymer of claim 1, wherein R′ is

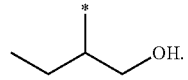 [SMILES: *C(CC)CO]

29. The polymer of claim 1, wherein R′ is

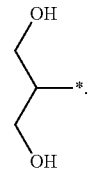

30. The polymer of claim 1, wherein R' is
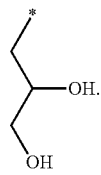
31. The composition of claim 17, wherein R' is
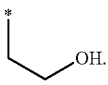
32. The composition of claim 17, wherein R' is
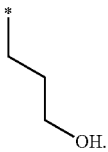
33. The composition of claim 17, wherein R' is
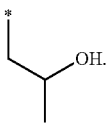
34. The composition of claim 17, wherein R' is
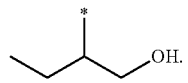
35. The composition of claim 17, wherein R' is
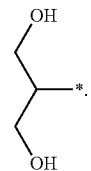
36. The composition of claim 17, wherein R' is
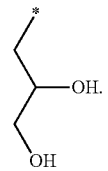
* * * * *